United States Patent
Lee et al.

(10) Patent No.: US 11,041,945 B2
(45) Date of Patent: Jun. 22, 2021

(54) ULTRASONIC DIAGNOSTIC APPARATUS AND METHOD FOR CONTROLLING ULTRASONIC PROBE TO TRANSMIT A PLURALITY OF PLANE WAVE SETS AT A PLURALITY OF STEERING ANGLES SO THAT A GRATING LOBE IS OUTSIDE A REGION OF INTEREST

(71) Applicants: SAMSUNG ELECTRONICS CO., LTD., Gyeonggi-do (KR); SOGANG UNIVERSITY RESEARCH FOUNDATION, Seoul (KR)

(72) Inventors: Hyun-taek Lee, Seoul (KR); Tai-kyong Song, Seoul (KR); Kang-won Jeon, Yongin-si (KR); Yong-sup Park, Seoul (KR); Mun-kyeong Hwang, Suwon-si (KR); Sua Bae, Seoul (KR)

(73) Assignees: Samsung Electronics Co., Ltd., Suwon-si (KR); Sogang University Research Foundation, Seoul (KR)

( * ) Notice: Subject to any disclaimer, the term of this patent is extended or adjusted under 35 U.S.C. 154(b) by 404 days.

(21) Appl. No.: 15/541,990

(22) PCT Filed: Feb. 2, 2016

(86) PCT No.: PCT/KR2016/001104
§ 371 (c)(1),
(2) Date: Jul. 6, 2017

(87) PCT Pub. No.: WO2016/129842
PCT Pub. Date: Aug. 18, 2016

(65) Prior Publication Data
US 2018/0017669 A1 Jan. 18, 2018

Related U.S. Application Data

(60) Provisional application No. 62/114,192, filed on Feb. 10, 2015.

(30) Foreign Application Priority Data

Sep. 22, 2015 (KR) .................. 10-2015-0133882

(51) Int. Cl.
*A61B 8/00* (2006.01)
*G01S 15/89* (2006.01)
(Continued)

(52) U.S. Cl.
CPC .......... *G01S 7/52085* (2013.01); *A61B 8/145* (2013.01); *A61B 8/4405* (2013.01);
(Continued)

(58) Field of Classification Search
None
See application file for complete search history.

(56) References Cited

U.S. PATENT DOCUMENTS 8,068,647 B2 11/2011 Lin
8,834,374 B2 9/2014 Shin
(Continued)

FOREIGN PATENT DOCUMENTS

JP 2006-346459 A 12/2006
KR 10-2010-0025102 A 3/2010
(Continued)

OTHER PUBLICATIONS

Montaldo et al., "Coherent Plane-Wave Compounding for Very High Frame Rate Ultrasonography and Transient Elastography" IEEE Transactions on Ultrasonics, Ferroelectrics, and Frequency Control, vol. 56, No. 3, Mar. 2009 (Year: 2009).*
(Continued)

*Primary Examiner* — Serkan Akar
*Assistant Examiner* — Aminah Asghar
(74) *Attorney, Agent, or Firm* — Jefferson IP Law, LLP

(57) ABSTRACT

Provided is an ultrasound diagnosis apparatus including a probe configured to transmit a plurality of plane waves at a
(Continued)

plurality of steering angles and a controller configured to determine the plurality of plane waves so that a grating lobe of a synthetic transmit focusing beam pattern using the plurality of plane waves is located outside a region of interest.

15 Claims, 25 Drawing Sheets

(51) Int. Cl.
G01S 7/52 (2006.01)
A61B 8/14 (2006.01)
A61B 8/08 (2006.01)
G01S 15/42 (2006.01)

(52) U.S. Cl.
CPC .......... *A61B 8/4472* (2013.01); *A61B 8/5207* (2013.01); *A61B 8/54* (2013.01); *G01S 7/52036* (2013.01); *G01S 7/52046* (2013.01); *G01S 7/52049* (2013.01); *G01S 15/42* (2013.01); *G01S 15/8995* (2013.01)

(56) References Cited

U.S. PATENT DOCUMENTS

| | | | |
|---|---|---|---|
| 9,642,590 B2 | 5/2017 | Hyun et al. | |
| 2003/0125628 A1* | 7/2003 | Song | G01S 15/8997 600/447 |
| 2005/0099887 A1* | 5/2005 | Zimmerman | G01S 7/52003 367/12 |
| 2005/0131298 A1* | 6/2005 | Cai | G01S 7/52047 600/447 |
| 2008/0194958 A1 | 8/2008 | Lee et al. | |
| 2009/0234230 A1* | 9/2009 | Bercoff | G01S 7/52049 600/447 |
| 2011/0172538 A1 | 7/2011 | Sumi | |
| 2013/0331699 A1* | 12/2013 | Ishihara | A61B 8/48 600/443 |
| 2014/0135625 A1* | 5/2014 | Konofagou | A61B 8/0883 600/443 |
| 2014/0148699 A1 | 5/2014 | Shim et al. | |
| 2014/0160882 A1* | 6/2014 | Vu | G01V 1/006 367/7 |
| 2014/0371594 A1* | 12/2014 | Flynn | A61B 8/463 600/454 |
| 2015/0087991 A1* | 3/2015 | Chen | G01S 7/5202 600/459 |

FOREIGN PATENT DOCUMENTS

| | | |
|---|---|---|
| KR | 10-2011-0021028 A | 3/2011 |
| KR | 10-2014-0069664 A | 6/2014 |

OTHER PUBLICATIONS

Alomari, Z., Harput, S., Hyder, S., & Freear, S. (2014). Selecting the number and values of the CPWI steering angles and the effect of that on imaging quality. 2014 IEEE International Ultrasonics Symposium (Year: 2014).*

"Jin Ho Chang, and Tai-Kyong Song", "A new synthetic aperture focusing method to suppress the diffraction of ultrasound", IEEE Transactions on Ultrasonics, Ferroelectrics and Frequency Control, vol. 58, No. 2, pp. 327-337, Analysis of Ultrasound Synthetic Transmit Focusing, Feb. 2011.

Jong Pil Lee, Jae Hee Song, and Tai-Kyong Song, "Analysis of Ultrasound Synthetic Transmit Focusing Using Plane Waves," The Journal of the Acoustical Society of Korea, vol. 33, No. 3, pp. 200-209, http://dx.doi.org/10.7776/ASK.2014.33.3.200, 2014.

* cited by examiner

ULTRASONIC DIAGNOSTIC APPARATUS AND METHOD FOR CONTROLLING ULTRASONIC PROBE TO TRANSMIT A PLURALITY OF PLANE WAVE SETS AT A PLURALITY OF STEERING ANGLES SO THAT A GRATING LOBE IS OUTSIDE A REGION OF INTEREST

TECHNICAL FIELD

The present disclosure relates to ultrasound diagnosis apparatuses, ultrasound probes, and methods of controlling the ultrasound probes, and more particularly, to ultrasound diagnosis apparatuses, ultrasound probes, and methods of controlling the ultrasound probes, which may improve the quality of ultrasound images.

BACKGROUND ART

Ultrasound diagnosis apparatuses transmit ultrasound signals generated by transducers of a probe to an object and receive echo signals reflected from the object, thereby obtaining at least one image of an internal part of the object (e.g., soft tissues or blood flow). In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound diagnosis apparatuses are widely used together with other image diagnosis apparatuses including a computed tomography (CT) apparatus, a magnetic resonance imaging (MRI) apparatus, and the like.

DETAILED DESCRIPTION OF THE INVENTION

Technical Solution

According to an aspect of an exemplary embodiment, an ultrasound diagnosis apparatus includes a probe configured to transmit a plurality of plane waves at a plurality of steering angles and a controller configured to determine the plurality of plane waves so that a grating lobe of a synthetic transmit focusing beam pattern using the plurality of plane waves is located outside a region of interest.

Advantageous Effects of the Invention

Provided are ultrasound diagnosis apparatuses, ultrasound probes, and methods of controlling the ultrasound probes which may improve the quality of ultrasound images.

BEST MODE

Figure 1:
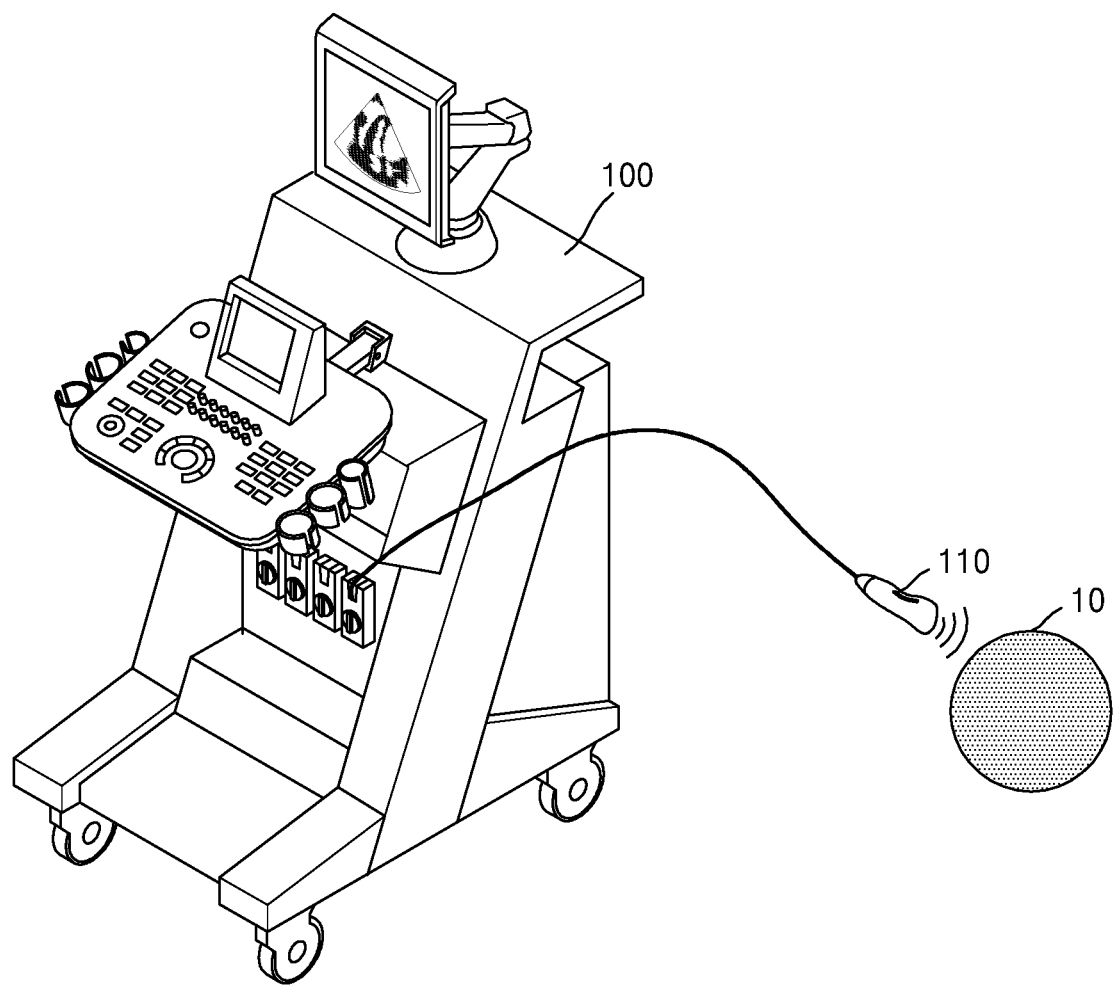
FIG. 1 is a view for explaining an ultrasound diagnosis apparatus according to some exemplary embodiments.

According to an aspect of an exemplary embodiment, an ultrasound diagnosis apparatus includes: a probe configured to transmit a plurality of plane waves at a plurality of steering angles; and a controller configured to determine the plurality of plane waves so that a grating lobe of a synthetic transmit focusing beam pattern using the plurality of plane waves is located outside a region of interest.

The controller may determine the plurality of plane waves so that an interval between sine values of the plurality of steering angles is equal to or less than a first reference value.

The controller may set a value obtained by dividing a wavelength by a size of an aperture of the probe as the first reference value.

The controller may fix a minimum steering angle and a maximum steering angle, and may determine the plurality of plane waves so that a number of the plurality of steering angles is equal to or greater than a second reference value.

The controller may adjust a size of the region of interest so that the size of the region of interest is less than a position of the grating lobe.

The probe may receive echo signals, and the controller may apply an apodization window having a low side lobe to the echo signals.

The controller may determine the plurality of plane waves so that an intensity of a grating lobe is less than an intensity of a main lobe in the synthetic transmit focusing beam pattern using the plurality of plane waves.

The plurality of plane waves determined by the controller may include a plurality of plane wave sets, and grating lobes of the plurality of plane wave sets do not overlap one another.

The plurality of plane waves determined by the controller may include a plurality of plane wave sets, and intervals between sine values of the plurality of steering angles of the plurality of plane wave sets are different from one another.

The plurality of plane waves determined by the controller may include a plurality of plane wave sets, minimum steering angles and maximum steering angles of the plurality of plane wave sets are the same, and numbers of the steering angles of the plurality of plane wave sets are different from one another.

The plurality of steering angles of the plurality of plane waves determined by the controller may be arbitrary.

The plurality of plane waves determined by the controller may include a plurality of plane wave sets, and intervals of the plurality of steering angles of the plurality of plane wave sets may be different from one another.

The probe may receive echo signals, and the controller may apply an apodization window having a low side lobe to the echo signals.

The controller may determine the plurality of plane waves so that the grating lobe is located outside a region of interest.

According to an aspect of another exemplary embodiment, an ultrasound probe includes: an ultrasound transceiver configured to transmit a plurality of plane waves at a plurality of steering angles; and a controller configured to control the ultrasound transceiver so that a grating lobe of a synthetic transmit focusing beam pattern using the plurality of plane waves is located outside a region of interest.

The ultrasound transceiver may receive echo signals, and the controller may apply an apodization window having a low side lobe to the echo signals.

According to an aspect of another exemplary embodiment, an ultrasound probe includes: an ultrasound transceiver configured to transmit a plurality of plane waves at a plurality of steering angles; and a controller configured to determine the plurality of plane waves so that an intensity of a size of a grating lobe is less than an intensity of a main lobe in a synthetic transmit focusing beam pattern using the plurality of plane waves and to control the ultrasound transceiver to transmit the determined plurality of plane waves.

According to an aspect of another exemplary embodiment, a method of controlling an ultrasound probe includes: determining a plurality of plane waves so that a grating lobe of a synthetic transmit focusing beam pattern using the plurality of plane waves to be transmitted by the ultrasound probe at a plurality of steering angles is located outside a region of interest; and transmitting, by the ultrasound probe, the determined plurality of plane waves.

According to an aspect of another exemplary embodiment, a method of controlling an ultrasound probe includes: determining a plurality of plane waves so that an intensity of a grating lobe is less than an intensity of a main lobe in a synthetic transmit focusing beam pattern using the plurality of plane waves to be transmitted by the ultrasound probe at a plurality of steering angles; and transmitting, by the ultrasound probe, the determined plurality of plane waves.

Mode of the Invention

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

When a part "includes" or "comprises" an element, unless there is a particular description contrary thereto, the part can further include other elements, not excluding the other elements. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Some exemplary embodiments will now be explained with the accompanying drawings.

FIG. 1 is a view for explaining an ultrasound diagnosis apparatus 100 according to some exemplary embodiments.

Referring to FIG. 1, the ultrasound diagnosis apparatus 100 includes a probe 110. Although the ultrasound diagnosis apparatus 100 is connected to the probe 110 by wire in FIG. 1, the ultrasound diagnosis apparatus 100 may be wirelessly connected to the probe 110. Although the ultrasound diagnosis apparatus 100 is connected to only one probe 110 in FIG. 1, the ultrasound diagnosis apparatus 100 may be connected to a plurality of probes by wire or wirelessly.

The ultrasound diagnosis apparatus 100 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 110 transmits ultrasound signals to an object 10 and receives echo signals reflected from the object 10. The probe 110 may include a plurality of transducers. The plurality of transducers oscillate in response to electric signals and generate ultrasound waves that are acoustic energy. The probe 110 according to some exemplary embodiments may transmit ultrasound signals as plane waves.

The ultrasound diagnosis apparatus 100 may generate ultrasound data from the echo signals. The ultrasound diagnosis apparatus 100 may generate an ultrasound image based on the ultrasound data. The ultrasound diagnosis apparatus 100 may further include a display that may display the ultrasound image. A user may diagnose the object 10 by seeing the ultrasound image displayed by the ultrasound diagnosis apparatus 100.

Figure 2:
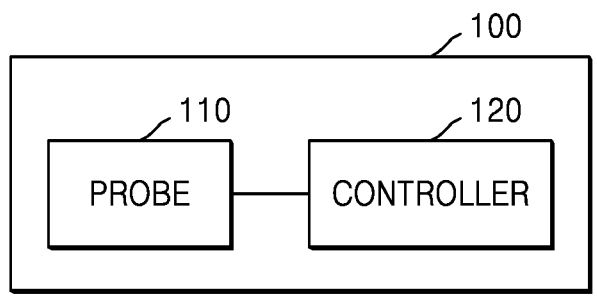
FIG. 2 is a block diagram showing a configuration of the ultrasound apparatus according to some exemplary embodiments.

FIG. 2 is a block diagram showing a configuration of the ultrasound diagnosis apparatus 100 according to some exemplary embodiments.

Referring to FIG. 2, the ultrasound diagnosis apparatus 100 includes the probe 110 and a controller 120.

The probe 110 may transmit ultrasound signals as plane waves to an object. The probe 110 may receive echo signals reflected from the object. The probe 110 may transmit a plurality of plane waves. In this case, the probe 110 may transmit the plurality of plane waves so that angles between the probe 110 and the plurality of plane waves are different from one another. Hereinafter, an angle between a plane wave and the probe 110 is referred to as a "steering angle". For example, the probe 110 may transmit a plurality of plane waves as shown in FIG. 3.

Figure 3:
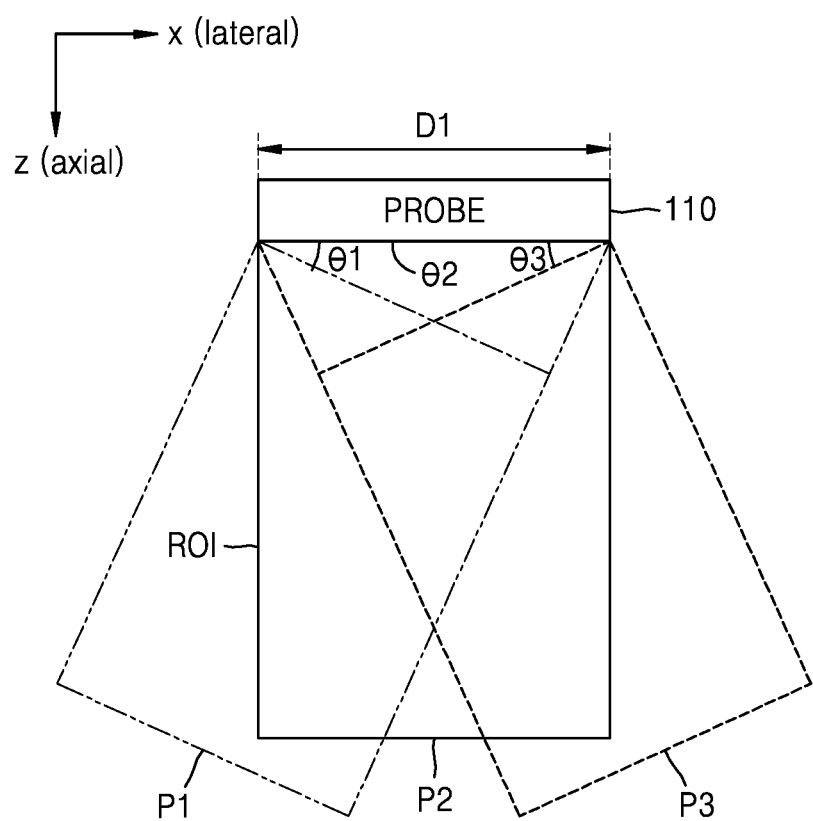
FIG. 3 is a view of a plurality of plane waves transmitted by a probe, according to some exemplary embodiments.

FIG. 3 is a view of a plurality of plane waves transmitted by the probe 110 according to some exemplary embodiments.

Referring to FIG. 3, the probe 110 may transmit a plurality of plane waves, for example, first through third plane waves P1, P2, and P3, at a plurality of angles, for example, first through third steering angles θ1, θ2, and θ3. In FIG. 3, the x-axis represents a lateral direction and the z-axis represents an axial direction that is a depth direction of an object.

The first through third steering angles θ1, θ2, and θ3 between the probe 110 and the first through third plane waves P1, P2, and P3 are different from one another. The probe 110 may transmit the first plane wave P1 at the first steering angle θ1, may transmit the second plane wave P2 at the second steering angle θ2, and may transmit the third plane wave P2 at the third steering angle θ3. The second steering angle θ2 may be 0°. The probe 110 may sequentially transmit the first through third plane waves P1, P2, and P3.

Although three plane waves, that is, the first through third plane waves P1, P2, and P3, are exemplarily illustrated in FIG. 3, the number of plane waves transmitted by the probe 110 or steering angles are not limited.

A region of the object to which the second plane wave P2 whose steering angle with the probe 110 is 0°, that is, that is not steered, is emitted may be referred to as a region of interest (ROI). The ROI may be a region where plane waves are maintained. A region outside the ROI may be a region where transmission of ultrasound waves transmitted from the probe 110 is limited and reception of echo signals is limited. Alternatively, the ROI may be a region of the object that is imaged.

A size of the ROI may be determined according to a size D1 of an aperture of the probe 110. The size D1 of the aperture of the probe 110 may be determined by a length of the probe 110. Alternatively, the size D1 of the aperture of the probe 110 may be determined by the number of transducers that transmit plane waves among a plurality of transducers included in the probe 110. Alternatively, when a region smaller than the size D1 of the aperture of the probe 110 is imaged, a size of the ROI may be less than the size D1 of the aperture of the probe 110.

Referring back to FIG. 2, the controller 120 may determine a plurality of plane waves to be transmitted by the probe 110. The controller 120 may control the probe 110 to transmit the determined plurality of plane waves. The controller 120 may apply a driving signal to the probe 110. The probe 110 may transmit the plurality of plane waves to the object according to the driving signal received from the controller 120.

The controller 120 may receive echo signals from the probe 110. The controller 120 may generate ultrasound data by focusing the echo signals. Also, the controller 120 may generate an ultrasound image based on the ultrasound data.

The controller 120 according to some exemplary embodiments may determine the plurality of plane waves so that grating lobes of the plurality of plane waves are suppressed. Also, the controller 120 may focus the echo signals so that the grating lobes are suppressed.

Before explaining a method performed by the controller 120 to suppress grating lobes according to some exemplary embodiments, a synthetic transmit focusing beam pattern using a plurality of plane waves will now be explained with reference to FIGS. 4 through 6.

Figure 4:
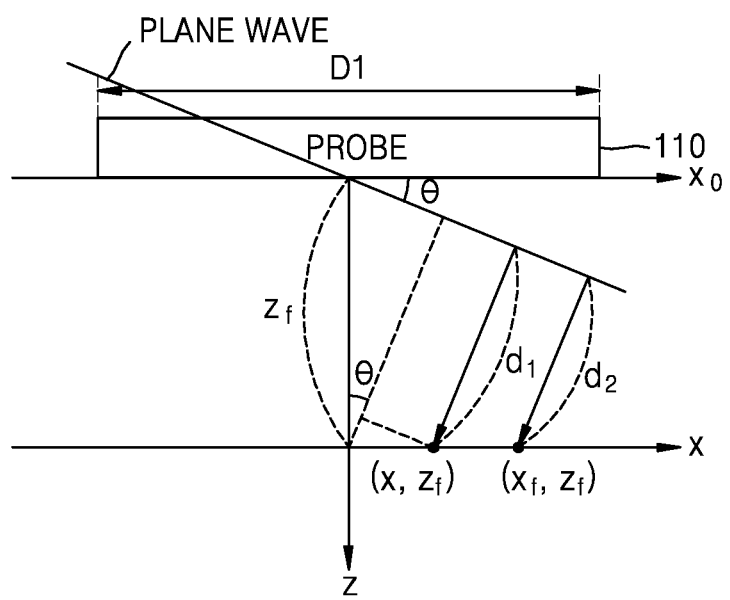
FIG. 4 is a view for explaining a synthetic transmit focusing beam pattern at one point in a region of interest (ROI), according to some exemplary embodiments.

FIG. 4 is a view for explaining a synthetic transmit focusing beam pattern at one point in an ROI according to some exemplary embodiments.

Referring to FIG. 4, the probe 110 transmits a plane wave at a steering angle θ. A transmit beam pattern formed at one point (x, $z_f$) in an ROI may be defined as in Equation 1.

$$\Phi_\theta^t(x,z_f) = e^{-j\omega t} e^{jkd_1}, d_1 = z_f \cos\theta - x \sin\theta, k = 2\pi/\lambda \quad \text{[Equation 1]}$$

In Equation 1, k is a wave number, λ is a wavelength, and $d_1$ is a distance by which a plane wave propagates to the point (x, $z_f$).

The transmit beam pattern of Equation 1 may be modified as in Equation 2.

$$\Phi_\theta^t(x,z_f) = \Phi_\alpha^t(x,z) = e^{-j\omega t} e^{jkz\beta} e^{-jkx\alpha}, \alpha = \sin\theta, \beta = \cos\theta, \alpha^2 + \beta^2 = 1 \quad \text{[Equation 2]}$$

As described with reference to FIG. 3, the probe 110 transmits a plurality of plane waves at a plurality of steering angles. Each of the plurality of plane waves transmitted by the probe 110 may be represented by using a plane wave angle function A(α). The plane wave angle function A(α) is an intensity of a plane wave with respect to a sine value of a steering angle that is used to transmit the plurality of plane waves.

A focal point ($x_f$, $z_f$) of FIG. 4 may be an arbitrary point at which imaging is to be performed. When a transmit delay used for each plane wave during synthetic transmit focusing at the focal point $(x_f, z_f)$ is $\tau(x_f, z_f, \alpha)$, a synthetic transmit focusing beam pattern may be defined as in Equation 3.

$$\Phi^t(x,z_f) = \int_{-\infty}^{\infty} A(\alpha)\tau(x_f,z_f,\alpha)\Phi_\alpha{}^t(x,z)d\alpha \qquad \text{[Equation 3]}$$

Since a distance d2 by which the plane wave propagates to the focal point (xf, zf) has to be compensated for by using the transmit delay, the transmit delay may be defined as in Equation 4.

$$\tau(x_f,z_f,\alpha) = e^{-jkd2} = e^{-jk(z_f\cos\theta - x_f\sin\theta)} = e^{-jkz_f\beta} e^{jkx_f\alpha} \qquad \text{[Equation 4]}$$

When Equation 2 and Equation 4 are input to Equation 3, Equation 5 may be obtained.

$$\Phi^t(x, z_f) = \qquad \text{[Equation 5]}$$

$$e^{-j\omega t}\int_{-\infty}^{\infty} A(\alpha)e^{-j2\pi\frac{x-x_f}{\lambda}}d\alpha = e^{-j\omega t} FT[A(\alpha)]\Big|_{f_x = \frac{x-x_f}{\lambda}}$$

In Equation 5, FT[•] is Fourier transform.

Figure 5:
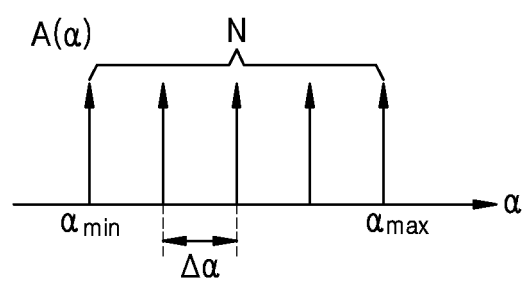
FIG. 5 is a graph showing a plane wave angle function according to some exemplary embodiments.

FIG. 5 is a graph showing a plane wave angle function according to some exemplary embodiments.

Referring to FIG. 5, a plane wave angle function $A(\alpha)$ is an intensity of a plane wave with respect to a sine value ($\alpha = \sin\theta$) of a steering angle $\theta$ used to transmit a plurality of plane waves. The plane wave angle function $A(\alpha)$ may be defined as in Equation 6.

$$A(\alpha) = \Sigma_{n=0}^{N-1}\delta(\alpha - \alpha_n) \qquad \text{[Equation 6]}$$

In Equation 6, N is the number of steering angles used to transmit a plurality of plane waves, and a total number of times synthesis occurs. N may be the number of plane waves. A sine value cm of each steering angle may be defined as in Equation 7.

$$\alpha_n = \alpha_{min} + \Delta\alpha \cdot n, (n=0,1,2,\ldots,N-1) \qquad \text{[Equation 7]}$$

$\alpha_{min}$ is a minimum value among sine values of steering angles. That is, $\alpha_{min}$ is a sine value of a minimum angle among the steering angles. $\alpha_{N-1}$ is a maximum value $\alpha_{max}$ among sine values of steering angles. That is, $\alpha_{max}$ is a sine value of a maximum angle among the steering angles.

$\Delta\alpha$ is an interval between sine values of a plurality of steering angles. $\Delta\alpha$ may be a difference between sine values of adjacent steering angles. In FIG. 5, $\Delta\alpha$ is constant. In FIG. 5, in order to transmit plane waves, steering angles having sine values between which intervals are constant are used.

When a plane wave angle function defined in Equations 6 and 7 is used, steering angles of a plurality of plane waves transmitted by the probe 110 are arcsin $\alpha_0$, arcsin $\alpha_2$, arcsin $\alpha_3$, . . . , and arcsin $\alpha_{N-1}$.

When a plane wave angle function defined in Equations 6 and 7 is used, a synthetic transmit focusing beam pattern may be defined as in Equation 8.

$$\psi^t(x', z_f) = c_0 \frac{\sin(kx' N_\alpha \Delta\alpha/2)}{\sin(kx' \Delta\alpha/2)} \qquad \text{[Equation 8]}$$

In Equation 8, $c_0$ and x' are respectively defined as in Equations 9 and 10.

$$c_0 = e^{-jkx'(\alpha_{min}+(N_\alpha-1)\Delta\alpha/2)} \qquad \text{[Equation 9]}$$

$$x' = x - x_f \qquad \text{[Equation 10]}$$

Figure 6:
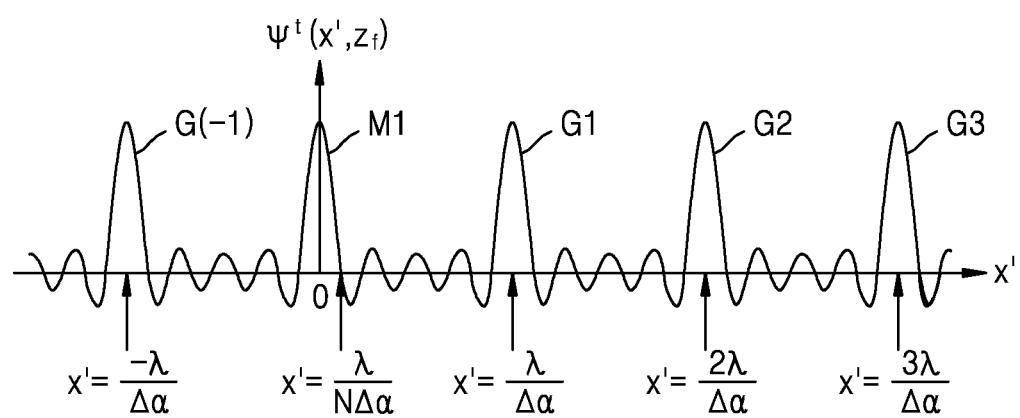
FIG. 6 is a graph showing a synthetic transmit focusing beam pattern according to some exemplary embodiments.

FIG. 6 is a graph showing a synthetic transmit focusing beam pattern according to some exemplary embodiments.

The graph of FIG. 6 shows a synthetic transmit focusing beam pattern along an x'-axis using a focal point $(x_f, z_f)$ as the center according to some exemplary embodiments. The synthetic transmit focusing beam pattern of FIG. 6 may be obtained by using Equation 8.

Referring to FIG. 6, a main lobe M1 is located at the focal point $(x_f, z_f)$ where x'=0. Since a width of the main lobe M1 is constant irrespective of an axial distance, the quality of an ultrasound image may be improved.

Grating lobes G1, G2, G3, and G4 are located at predetermined intervals from the main lobe M1 in the synthetic transmit focusing beam pattern. An intensity of each of the grating lobes G1, G2, G3, and G4 is the same as an intensity of the main lobe M1. A position of each of the grating lobes G1, G2, G3, and G4 may be defined as in Equation 11.

$$x' = \frac{2\pi n}{k\Delta\alpha} = \frac{\lambda}{\Delta\alpha}n, (n \text{ is the integer}) \qquad \text{[Equation 11]}$$

Ultrasound waves having an intensity of the main lobe M1 are reflected at the focal point $(x_f, z_f)$, and echo signals reflected from the focal point $(x_f, z_f)$ are received through the probe 110. The controller 120 may generate ultrasound data by focusing the echo signals. The quality of an ultrasound image may increase as ultrasound waves are more strongly focused on the focal point $(x_f, z_f)$. However, an ultrasound beam is strongly focused on points other than the focal point $(x_f, z_f)$ due to the grating lobes G(−1), G1, G2, and G3, and thus ultrasound waves having a high intensity are reflected from the points other than the focal point $(x_f, z_f)$. Echo signals having a high intensity reflected from the points other than the focal point $(x_f, z_f)$ reduce the quality of an ultrasound image. This is because a signal-to-noise ratio (SNR) and a contrast ratio of an ultrasound image may be reduced due to the grating lobes G(−1), G1, G2, and G3 and artifacts may occur on the ultrasound image.

As described above, the controller 120 according to some exemplary embodiments may determine a plurality of plane waves so that grating lobes of the plurality of plane waves are suppressed. A method performed by the controller 120 to suppress grating lobes according to some exemplary embodiments will now be explained.

According to some exemplary embodiments, the controller 120 may determine a plurality of plane waves so that a grating lobe of a synthetic transmit focusing beam pattern is located outside an ROI, which will be referred to as a "first exemplary embodiment".

According to other exemplary embodiments, the controller 120 may determine a plurality of plane waves so that an intensity of a grating lobe is less than an intensity of a main lobe in a synthetic transmit focusing beam pattern using the plurality of plane waves. Next, the controller 120 may control the probe 110 to transmit the determined plurality of plane waves, which will be referred to as a "second exemplary embodiment".

First Exemplary Embodiment

A method performed by the controller 120 of the ultrasound diagnosis apparatus 100 to determine a plurality of plane waves so that a grating lobe of a synthetic transmit focusing beam pattern is located outside an ROI according to a first exemplary embodiment will now be explained with reference to FIGS. 7A through 10B.

In some exemplary embodiments, the controller 120 may adjust a plurality of steering angles for transmitting a plurality of plane waves so that a grating lobe is located outside an ROI.

Figure 7A:
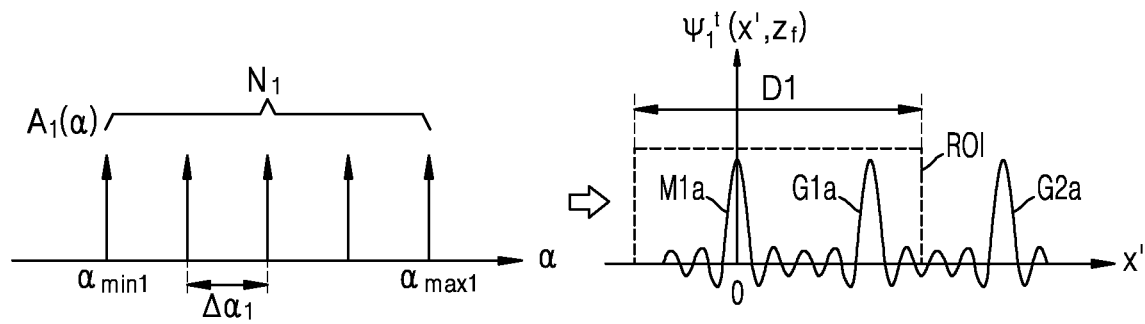
FIGS. 7A and 7B are graphs showing a synthetic transmit focusing beam pattern according to a plane wave angle function for explaining a relationship between a position of a grating lobe and a steering angle, according to some exemplary embodiments.
Figure 7B:
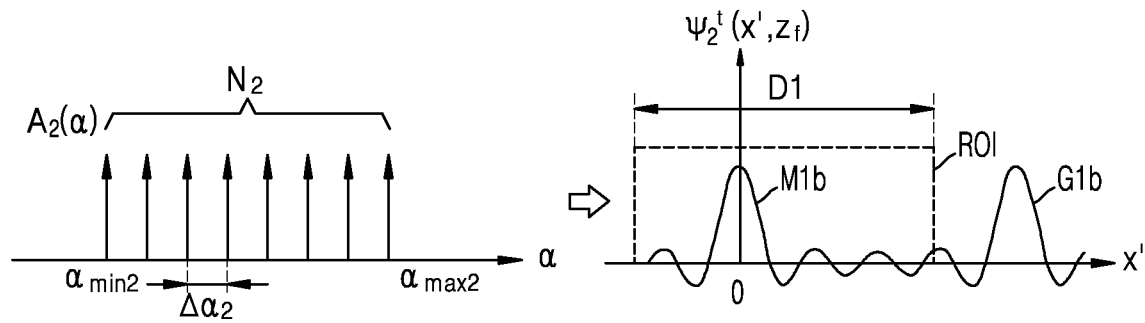

FIGS. 7A and 7B are graphs showing a synthetic transmit focusing beam pattern according to a plane wave angle function for explaining a relationship between a position of a grating lobe and a steering angle according to some exemplary embodiments. In FIGS. 7A and 7B, D1 is a size of an aperture of the probe 110. In FIGS. 7A and 7B, the size D1 of the aperture of the probe 110 is equal to a size of an ROI.

FIG. 7A is a graph showing a synthetic transmit focusing beam pattern when a plane wave angle function $A_1(\alpha)$ in which an interval between sine values of a plurality of steering angles is $\Delta\alpha_1$ is used. In FIG. 7A, a grating lobe G1$a$ of the synthetic transmit focusing beam pattern is located inside the ROI.

FIG. 7B is a graph showing a synthetic transmit focusing beam pattern when a plane wave angle function $A_2(\alpha)$ in which an interval between sine values of a plurality of steering angles is $\Delta\alpha_2$ is used. In FIG. 7B, the interval $\Delta\alpha_2$ is less than the interval $\Delta\alpha_1$. In FIG. 7B, an ROI is the same as the ROI of FIG. 7A. In FIG. 7B, a grating lobe G1$b$ of the synthetic transmit focusing beam pattern is located outside the ROI.

Referring to Equation 11, it is found that a position of a grating lobe along an x'-axis in a synthetic transmit focusing beam pattern is inversely proportional to an interval $\Delta\alpha$ that is an interval between sine values of a plurality of steering angles. Accordingly, it is found that as the interval $\Delta\alpha$ decreases, the position of the grating lobe is farther from a position (x'=0) of a main lobe. Accordingly, when the interval $\Delta\alpha$ is adjusted so that a position of a grating lobe that is the closest to the main lobe is greater than the size D1 of the aperture of the probe 110, the grating lobe may be located outside an ROI.

Accordingly, the controller 120 may determine a plurality of plane waves so that an interval $\Delta\alpha$ that is an interval between sine values of a plurality of steering angles is equal to or less than a first reference value, as in Equation 12.

$$\Delta\alpha \leq \frac{\lambda}{D1} \qquad \text{[Equation 12]}$$

According to Equation 12, the controller 120 may set a value obtained by dividing a wavelength by the size of the aperture of the probe 110 as the first reference value. The controller 120 may determine a plurality of plane waves by adjusting a plurality of steering angles based on the interval $\Delta\alpha$ that is equal to or less than the first reference value. Accordingly, a grating lobe may be located outside the ROI.

As described with reference to FIGS. 7A and 7B, the controller 120 may allow a grating lobe to be located outside an ROI by adjusting a plurality of steering angles for transmitting a plurality of plane waves.

Alternatively, according to some exemplary embodiments, the controller 120 may allow a grating lobe to be located outside an ROI by adjusting the number of steering angles of a plurality of plane waves transmitted by the probe 110. This is because when $\alpha_{min}$ and $\alpha_{max}$ are fixed according to a minimum steering angle and a maximum steering angle, the interval $\Delta\alpha$ may be adjusted by adjusting the number N of steering angles.

As described with reference to FIG. 7B, $\alpha_{min2}$ and $\alpha_{max2}$ may be fixed according to a minimum steering angle, and a maximum steering angle and the number (e.g., $N_2$=9) of steering angles may be determined so that a grating lobe is located outside an ROI. The controller 120 may adjust the number of steering angles to be equal to or greater than a second reference value. The second reference value may be obtained by using Equation 13 that is a modification of Equation 12.

$$N \geq D1(\alpha_{max}-\alpha_{min})/\lambda+1 \qquad \text{[Equation 13]}$$

The controller 120 may determine a plurality of plane waves by adjusting a plurality of steering angles based on the number N of the steering angles that is equal to or greater than the second reference value and satisfies Equation 13. Accordingly, a grating lobe may be located outside an ROI.

According to some exemplary embodiments, the controller 120 may allow a grating lobe to be located outside an ROI by adjusting a size of the ROI.

Figure 8A:
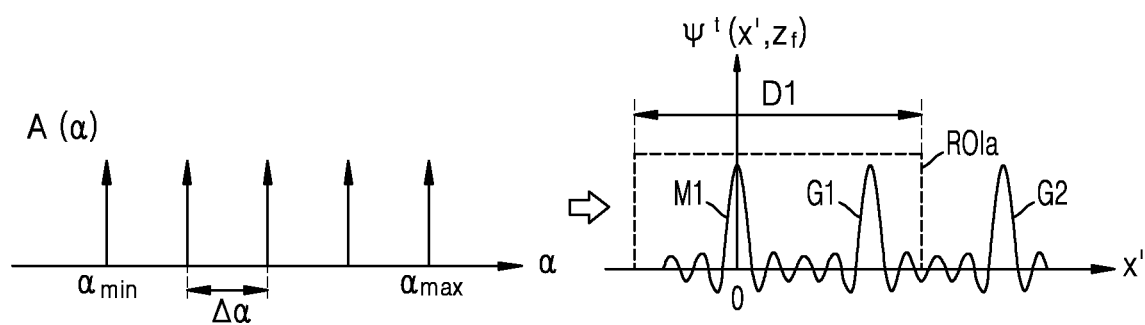
FIGS. 8A and 8B are graphs showing a synthetic transmit focusing beam pattern according to a plane wave angle function for explaining a relationship between a position of a grating lobe and a size of an ROI, according to some exemplary embodiments.
Figure 8B:
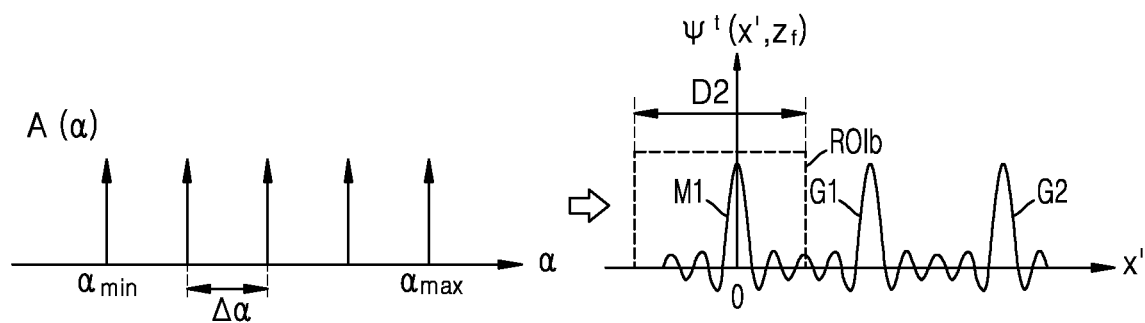

FIGS. 8A and 8B are graphs showing a synthetic transmit focusing beam pattern according to a plane wave angle function for explaining a relationship between a position of a grating lobe and a size of an ROI according to some exemplary embodiments.

In FIGS. 8A and 8B, plane wave angle functions are the same, and thus synthetic transmit focusing beam patterns are also the same. In both FIGS. 8A and 8B, intervals between sine values of a plurality of steering angles are $\Delta\alpha$. However, a size of an ROI (referred to as ROIa) in FIG. 8A is D1 and a size of an ROI (referred to as ROIb) in FIG. 8B is D2 which is less than D1. A grating lobe G1 is located inside the ROIa in FIG. 8A whereas the grating lobe G1 is located outside the ROIb in FIG. 8B.

Accordingly, when the size D2 of the ROIb is adjusted to be less than a position of the grating lobe G1 as shown in FIG. 8B, the grating lobe G1 may be located outside the ROIb. When the size D2 of the ROIb satisfies Equation 14, the grating lobe G1 may be located outside the ROIb.

$$D2 \leq \frac{\lambda}{\Delta\alpha} \qquad \text{[Equation 14]}$$

A size of an ROI may be determined by a size of an aperture of the probe 110. Accordingly, the controller 120 may adjust the size of the aperture of the probe 110 to be less than a position of a grating lobe. In detail, the size of the aperture of the probe 110 may be adjusted to satisfy Equation 12.

Alternatively, the controller 120 may limit a region that is to be imaged without adjusting the size of the aperture of the probe 110. For example, when the size of the aperture of the probe 110 is D1, a size of an ROI may be adjusted so that a size of the region that is to be imaged is determined to be D2 that is less than the size D1 of the aperture of the probe 110.

Exemplary embodiments in which a size of an aperture of the probe 110 is adjusted in order to adjust a size of an ROI will now be explained with reference to FIGS. 9A through 10B.

Figure 9A:
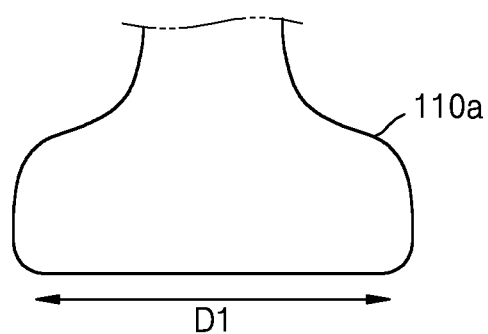
FIGS. 9A and 9B are views of probes having apertures with different sizes, according to some exemplary embodiments.
Figure 9B:
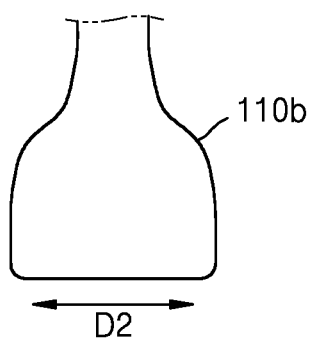

FIGS. 9A and 9B are views of probes having apertures with different sizes according to some exemplary embodiments.

Referring to FIG. 9A, a size of an aperture of a probe 110*a* is D1 and a size of an aperture of a probe 110*b* is D2. That is, a probe may be selected from among the plurality of probes 110*a* and 110*b* based on a size of an ROI to be adjusted. Referring to FIGS. 8A through 9B, the probe 110b whose aperture has the size D2 may be selected, a size of an ROIb may be adjusted to D2, and a grating lobe may be located outside the ROIb.

Figure 10A:
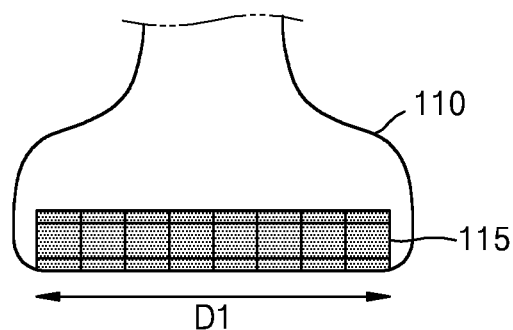
FIGS. 10A and 10B are views illustrating a case where a size of an aperture of a probe is adjusted by using a plurality of transducers included in the probe, according to some exemplary embodiments.
Figure 10B:
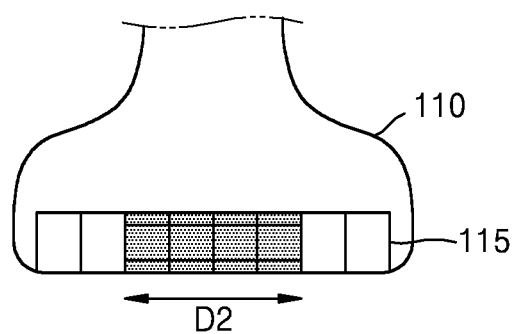

FIGS. 10A and 10B are views illustrating a case where a size of an aperture of the probe 110 is adjusted by using a plurality of transducers included in the probe 110 according to some exemplary embodiments.

Referring to FIGS. 10A and 10B, the probe 110 includes a plurality of transducers 115. A size of an aperture of the probe 110 may be adjusted according to the number of transducers for transmitting plane waves among the plurality of transducers 115 included in the probe 110.

In FIG. 10A, all of the transducers 115 included in the probe 110 transmit plane waves and a size of an aperture of the probe 110 is D1. In FIG. 10B, only some transducers among the transducers 115 included in the probe 110 transmit plane waves and a size of an aperture of the probe 110 is D2. In FIG. 10B, only four transducers among eight transducers 115 are activated.

Referring to FIGS. 8A and 8B and FIGS. 10A and 10B, a size of an ROIb may be adjusted to D2 and a grating lobe may be located outside the ROIb by adjusting the number of activated transducers so that a size of an aperture of the probe 110 is D2.

FIGS. 10A and 10B are exemplary views for convenience of explanation, and the number of transducers included in the probe 110 and the number of activated transducers are not limited thereto.

As shown in FIGS. 9A through 10B, a size of an ROI may be adjusted and a grating lobe may be located outside the ROI by adjusting a size of an aperture of the probe 110.

The first exemplary embodiment in which a grating lobe is located outside an ROI by adjusting one of a steering angle and a size of the ROI has been explained with reference to FIGS. 7A through 10B. The controller 120 of the ultrasound diagnosis apparatus 100 may allow a grating lobe to be located outside an ROI by adjusting one of a steering angle and a size of the ROI, or both the steering angle and the size of the ROI. That is, the controller 120 may allow a grating lobe to be located outside an ROI by adjusting at least one of a steering angle and a size of the ROI. Since a plane wave is not maintained in a region outside an ROI, normal synthetic focusing is not performed in the region outside the ROI. Accordingly, an intensity of a grating lobe may be reduced to be much less than an intensity of a main lobe and the quality of an ultrasound image may be improved.

Second Exemplary Embodiment

The controller 120 of the ultrasound diagnosis apparatus 100 may determine a plurality of plane waves that are plane waves combinations so that an intensity of a grating lobe is less than an intensity of a main lobe in a synthetic transmit focusing beam pattern using the plurality of plane waves according to a second exemplary embodiment. The plurality of plane waves determined by the controller 120 may include a plurality of plane wave sets, and grating lobes of the plurality of plane wave sets may not overlap one another.

A method of determining a plurality of plane waves so that an intensity of a grating lobe is less than an intensity of a main lobe according to the second exemplary embodiment will now be explained with reference to FIGS. 11A through 14B.

Figure 11A:
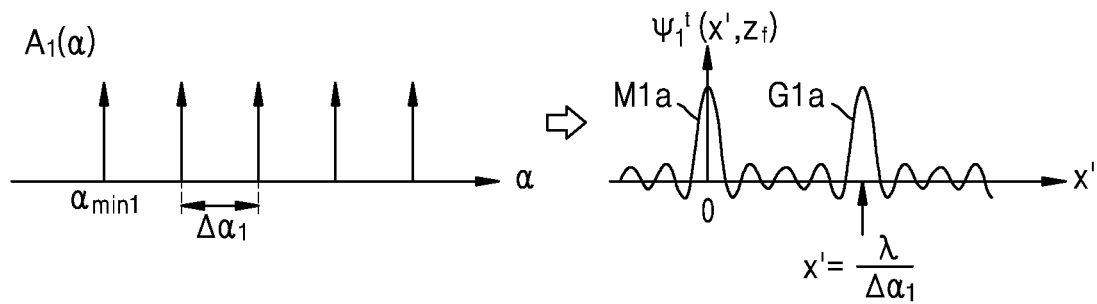
FIGS. 11A through 11C are graphs showing a case where a plurality of plane wave sets, in which intervals between sine values of a plurality of steering angles are different from one another, are used, according to some exemplary embodiments.
Figure 11B:
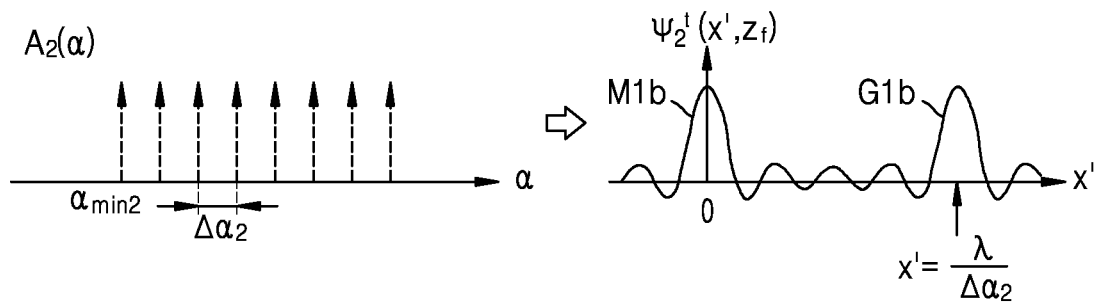
Figure 11C:
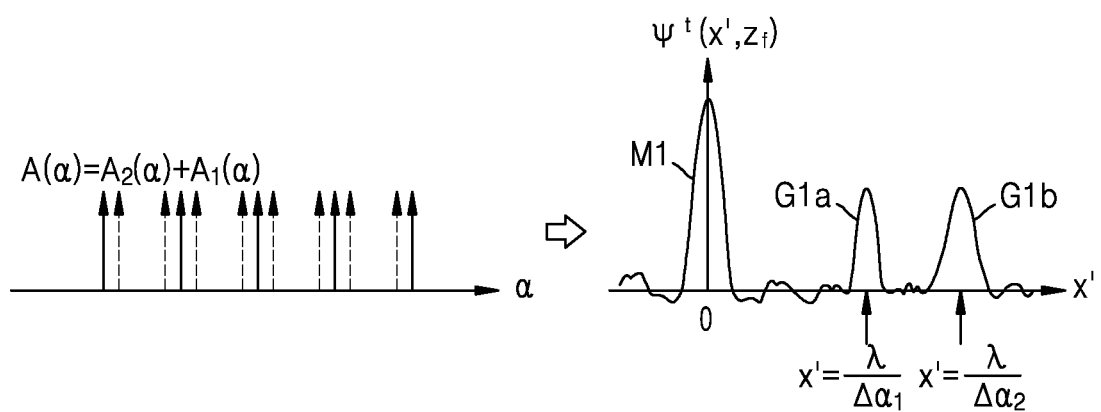

FIGS. 11A through 11C are graphs showing a case where a plurality of plane wave sets in which intervals between sine values of a plurality of steering angles are different from one another are used according to some exemplary embodiments.

FIG. 11A is a graph showing a first synthetic transmit focusing beam pattern when a first plane wave angle function $A_1(\alpha)$ in which an interval between sine values of a plurality of steering angles is $\Delta\alpha_1$ is used. FIG. 11B is a graph showing a second synthetic transmit focusing beam pattern when a plane wave angle function $A_2(\alpha)$ in which an interval between sine values of a plurality of steering angles is $\Delta\alpha_2$ is used.

Referring to FIGS. 11A and 11B, main lobes M1a and M1b are located at the same position (x'=0) whereas positions of grating lobes G1a and G1b do not overlap each other. This is because the intervals $\Delta\alpha_1$ and $\Delta\alpha_2$ between the sine values of the plurality of steering angles for determining the positions of the grating lobes G1a and G1b are different from each other.

When a plane wave angle function $A(\alpha)$ obtained by summing the first plane wave angle function $A_1(\alpha)$ and the second plane wave angle function $A_2(\alpha)$ is used as shown in FIG. 11C, a synthetic transmit focusing beam pattern is obtained by summing the first synthetic transmit focusing beam pattern of FIG. 11A and the second synthetic transmit focusing beam pattern of FIG. 11B. In the synthetic transmit focusing beam pattern of FIG. 11C, intensities of the grating lobes G1a and G1b are less than an intensity of a main lobe M1. Since the main lobe M1a in the first plane wave angle function $A_1(\alpha)$ and the main lobe M1b in the second plane wave angle function $A_2(\alpha)$ are located at the same position to overlap each other, that is, x'=0, an intensity of the main lobe M1 is increased. In contrast, since the grating lobe G1a in the first plane wave angle function $A_1(\alpha)$ and the grating lobe G1b in the second plane wave angle function $A_2(\alpha)$ do not overlap each other, intensities of the grating lobes G1a and G1b are less than an intensity of the main lobe M1.

That is, the controller 120 of the ultrasound diagnosis apparatus 100 may use a plurality of plane wave sets in which intervals $\Delta\alpha$ between sine values of a plurality of steering angles are different from one another as shown in FIGS. 11A through 11C. Although a plurality of plane waves include two plane wave sets in FIGS. 11A through 11C, some exemplary embodiments are not limited thereto. The plurality of plane waves may include three or more plane wave sets. The controller 120 may reduce an intensity of a grating lobe relative to a main lobe by using a plurality of intervals $\Delta\alpha$.

As shown in FIGS. 11A through 11C, a plurality of plane waves determined by the controller 120 may include a plurality of plane wave sets, and intervals between sine values of a plurality of steering angles for the plurality of plane wave sets may be different from one another.

Figure 12A:
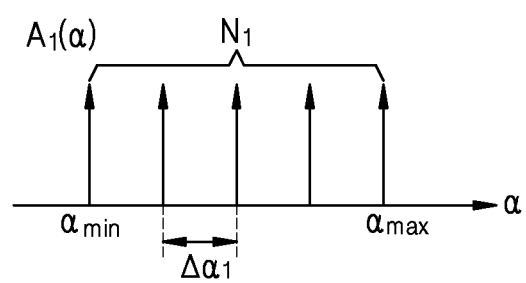
FIGS. 12A and 12B are graphs showing a case where a plurality of plane wave sets, in which intervals between sine values of a plurality of steering angles are different from one another, are used, according to other exemplary embodiments.
Figure 12B:
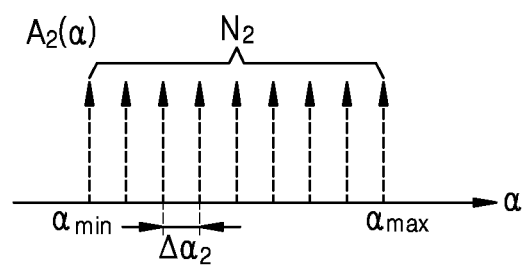

FIGS. 12A and 12B are graphs showing a case where a plurality of plane wave sets in which intervals between sine values of a plurality of steering angles are different from one another are used according to other exemplary embodiments.

Referring to FIGS. 12A and 12B, $\alpha_{min}$ and $\alpha_{max}$ of a first plane wave angle function $A_1(\alpha)$ and a second plane wave angle function $A_2(\alpha)$ are the same and the numbers $N_1$ and $N_2$ of steering angles included in the first and second plane wave angle functions $A_1(\alpha)$ and $A_2(\alpha)$ are different from each other. That is, although minimum steering angles and maximum steering angles of the first plane wave angle function $A_1(\alpha)$ and the second plane wave angle function $A_2(\alpha)$ are the same, the numbers $N_1$ and $N_2$ of the steering angles are different from each other. Accordingly, intervals $\Delta\alpha_1$ and $\Delta\alpha_2$ between sine values of the plurality of steering angles are different from each other.

When a plane wave angle function $A_1(\alpha)+A_2(\alpha)$ obtained by summing the first and second plane wave angle functions $A_1(\alpha)$ and $A_2(\alpha)$ in which the numbers $N_1$ and $N_2$ of the steering angles are different from each other are used, a plurality of plane wave angle functions in which the intervals $\Delta\alpha_1$ and $\Delta\alpha_2$ between sine values of a steering angles are different from each other may be used as shown in FIGS. 11A through 11C. Accordingly, the controller 120 may reduce an intensity of a grating lobe to be less than an intensity of a main lobe.

As shown in FIGS. 12A and 12B, a plurality of plane waves determined by the controller 120 may include a plurality of plane wave sets, minimum steering angles and maximum steering angles of the plurality of plane wave sets may be the same, and the numbers of steering angles of the plurality of plane wave sets may be different from one another.

Figure 13:
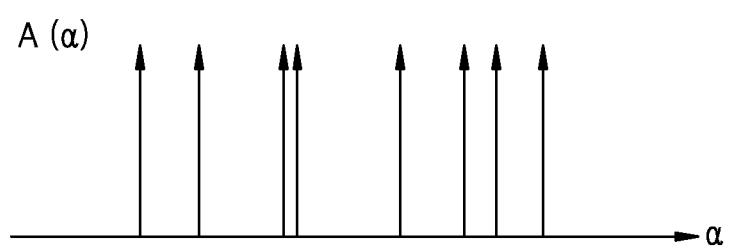
FIG. 13 is a graph showing a case where a plane wave angle function is formed by using sine values of arbitrary steering angles, according to some exemplary embodiments.

FIG. 13 is a graph showing a case where a plane wave angle function is formed by using sine values of arbitrary steering angles according to some exemplary embodiments.

Referring to FIG. 13, a plane wave angle function $A(\alpha)$ may be formed by using sine values $\alpha$ of arbitrary steering angles. Although a plane wave angle function in which intervals between sine values of steering angles are constant has been used in the previous exemplary embodiments, intervals between sine values of adjacent steering angles are not constant in FIG. 13.

As shown in FIG. 13, a plurality of steering angles of a plurality of plane waves determined by the controller 1250 may be arbitrary. Accordingly, the controller 120 may reduce an intensity of a grating lobe to be less than an intensity of a main lobe.

Figure 14A:
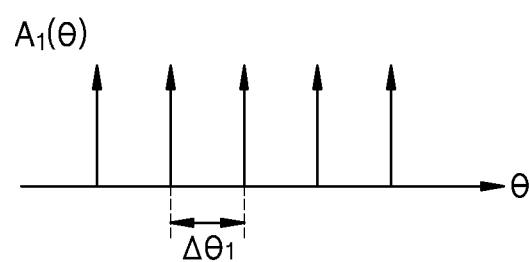
FIGS. 14A and 14B are graphs showing a case where a plurality of plane wave sets, in which intervals between steering angles are different from one another, are used, according to some exemplary embodiments.
Figure 14B:
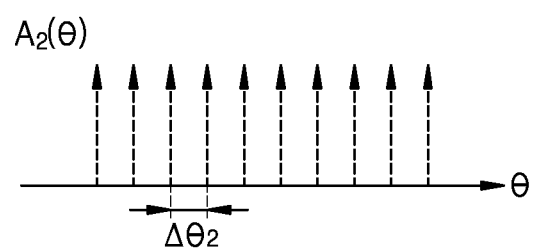

FIGS. 14A and 14B are graphs showing a case where a plurality of plane waves in which intervals between steering angles are different from one another are used according to some exemplary embodiments.

FIG. 14A shows a first plane wave angle function $A_1(\theta)$ in which an interval between steering angles, that is, a difference between adjacent steering angles, is a first angle $\Delta\theta_1$. FIG. 14B shows a second plane wave angle function $A_2(\theta)$ in which an interval between steering angles is a second angle $\Delta\theta_2$.

Accordingly, when a plane wave angle function obtained by summing the first plane wave angle function $A_1(\theta)$ and the second plane wave angle function $A_2(\theta)$ is used, it may be similar to a case where a plurality of plane wave sets (e.g., see FIGS. 11A through 11C) in which intervals between sine values of a plurality of steering angles are different from one another are used.

The second exemplary embodiment in which a plurality of plane waves are determined so that an intensity of a grating lobe is less than an intensity of a main lobe in a synthetic transmit focusing beam pattern using a plurality of plane waves has been described with reference to FIGS. 11A through 14B. A plurality of plane waves may be determined in various ways according to the second exemplary embodiment as shown in FIGS. 11A through 14B. Also, methods of FIGS. 11A through 14B may be used by being combined in various ways.

Also, according to methods other than the methods of FIGS. 11A through 14B, the controller 120 may determine a plurality of plane waves so that an intensity of a grating lobe is less than an intensity of a main lobe.

For example, the controller 120 may use different plane wave combinations whenever compounding for synthesizing a series of received ultrasound images is performed. Accordingly, the effect of a grating lobe during the compounding may be reduced.

Also, although the first exemplary embodiment in which a plurality of plane waves are determined so that a grating lobe is located outside an ROI and the second exemplary embodiment in which a plurality of plane waves are determined so that an intensity of a grating lobe is less than an intensity of a main lobe have been separately described, the first exemplary embodiment and the second exemplary embodiment may be used by being combined with each other.

As described above, the controller 120 of the ultrasound diagnosis apparatus 100 may determine a plurality of plane waves according to at least one of the first exemplary embodiment and the second exemplary embodiment. The controller 120 may control the probe 110 to transmit the determined plurality of plane waves.

The probe 110 may receive echo signals reflected from an object. The controller 120 may apply an apodization window to the echo signals received by the probe 110. In this case, the controller 12 may use an apodization window having a low side lobe. For example, an apodization window having a low side lobe such as a Hanning window or a Hamming window may be used. Accordingly, a grating lobe of the echo signals may be reduced.

Figure 15A:
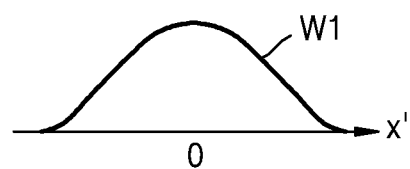
FIGS. 15A and 15B are graphs showing a Hanning window and a rectangular window, according to some exemplary embodiments.
Figure 15B:
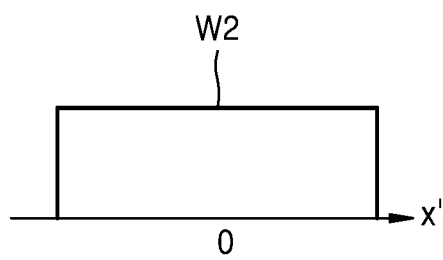

FIGS. 15A and 15B are graphs showing a Hanning window W1 and a rectangular window W2 according to some exemplary embodiments. In some exemplary embodiments, the controller 120 may apply the Hanning window W1 to echo signals received by the probe 110 as shown in FIG. 15A. Since the Hanning window W1, instead of the rectangular window W2, is used, an intensity of a grating lobe may be reduced compared to an intensity of a main lobe in the received echo signals.

An apodization window having a low side lobe such as a Hamming window, instead of the Hanning window W2 of FIG. 15A, may be used.

Figure 16A:
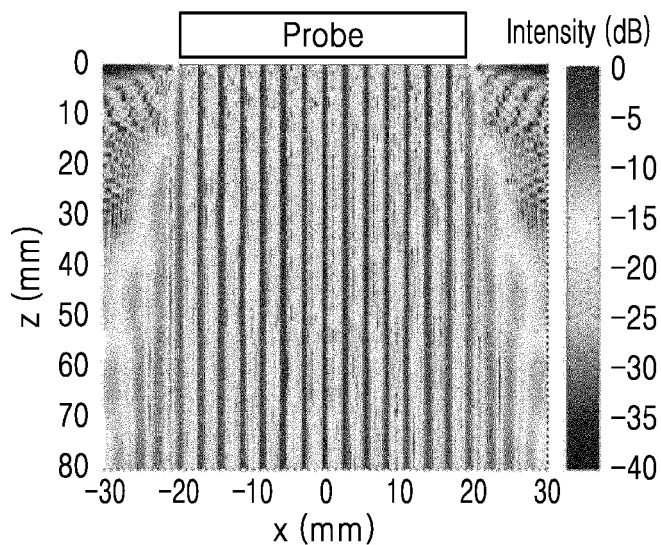
FIGS. 16A and 16B are views illustrating a simulation result for explaining an effect of a synthetic transmit focusing beam pattern in which a grating lobe is located outside an ROI, according to a first exemplary embodiment.
Figure 16B:
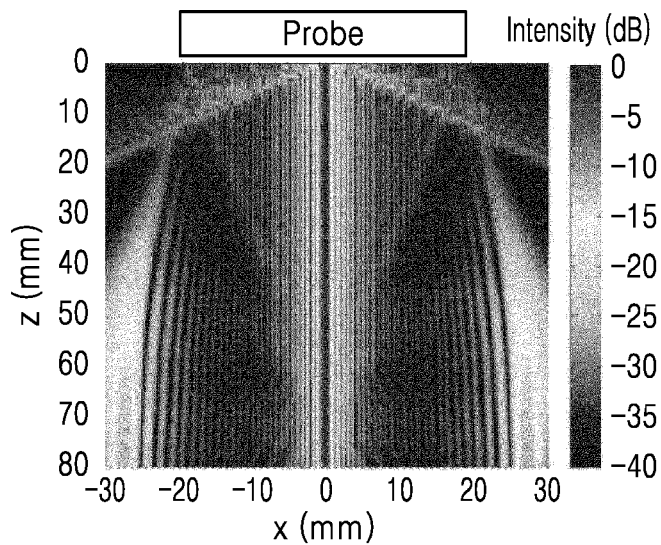

FIGS. 16A and 16B are views illustrating a simulation result for explaining the effect of a synthetic transmit focusing beam pattern in which a grating lobe is located outside an ROI according to the first exemplary embodiment. FIG. 16A is a view illustrating a simulation result of a synthetic transmit focusing beam pattern in which a grating lobe is located inside an ROI. FIG. 16B is a view illustrating a simulation result of a synthetic transmit focusing beam pattern in which a grating lobe is located outside an ROI.

FIG. 16A illustrates a synthetic transmit focusing beam pattern when a plurality of plane waves that are plane wave combinations having $\Delta\alpha=0.05$ (2.866°) and N=5 are used. An intensity of the synthetic transmit focusing beam pattern constantly increases within an ROI (−20 mm<x<20 mm) This is because grating lobes are located in the ROI (−20 mm<x<20 mm) in addition to a region (x=0) where a main lobe is located. Since the grating lobes are located in the ROI (−20 mm<x<20 mm) that is to be imaged, the quality of an ultrasound image is reduced.

FIG. 16B illustrates a synthetic transmit focusing beam pattern when a plurality of plane waves that are plane wave combinations having $\Delta\alpha=0.005$ (0.287°) and N=40 are used. An intensity of the synthetic transmit focusing beam pattern is not large in an ROI (−20 mm<x<20 mm) except in a region (x=0) where a main lobe is located. This is because grating lobes are located outside the ROI (−20 mm<x<20 mm) by reducing an interval $\Delta\alpha$. Since an ultrasound beam does not strongly reach a region outside the ROI (−20 mm<x<20 mm), an intensity of a grating lobe is reduced to be less than an intensity of the main lobe.

Figure 17A:
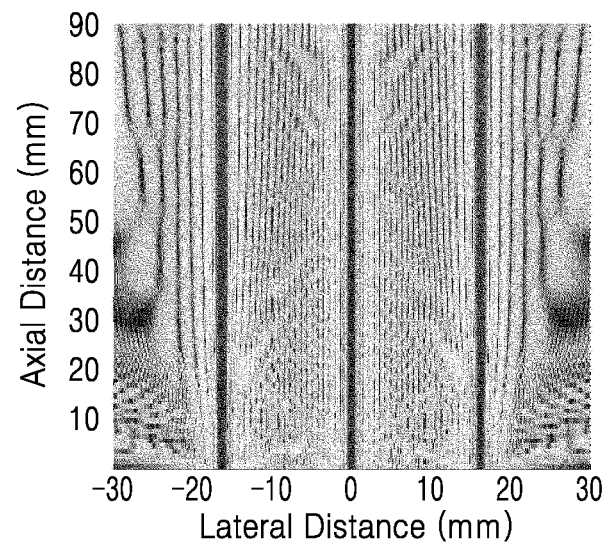
FIGS. 17A through 18B are views illustrating simulation results for explaining an effect of a synthetic transmit focusing beam pattern when a plane wave combination is used so that a size of a grating lobe is less than a size of a main lobe, according to a second exemplary embodiment.
Figure 17B:
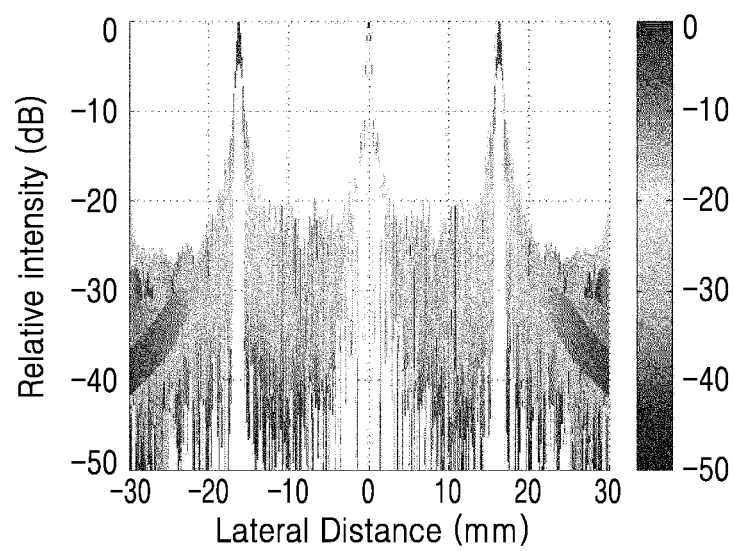
Figure 18A:
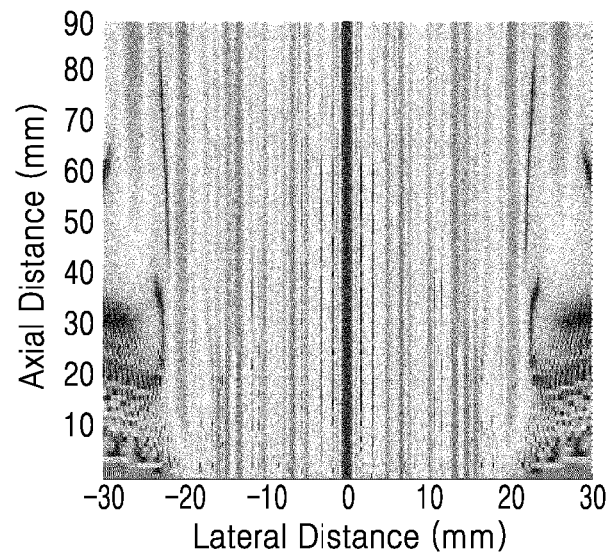
Figure 18B:
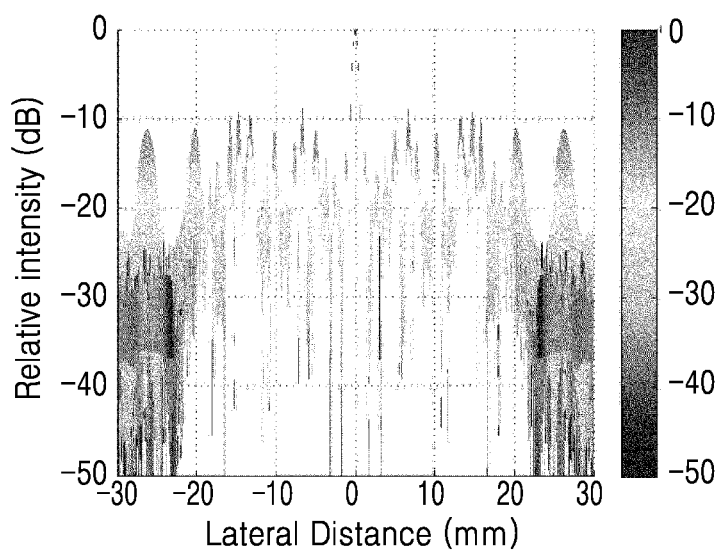

FIGS. 17A through 18B are views illustrating simulation results for explaining the effect of a synthetic transmit focusing beam pattern when a plane wave combination is used so that an intensity of a grating lobe is less than an intensity of a main lobe according to the second exemplary embodiment. FIGS. 17A and 17B illustrate a synthetic transmit focusing beam pattern when a plane wave combination using one interval Δα is used. FIGS. 18A and 18B illustrate a synthetic transmit focusing beam pattern when a plane wave combination using a plurality of intervals Δα is used.

FIGS. 17A and 17B illustrate a synthetic transmit focusing beam pattern when a plane wave combination having Δα=0.019 (1.083°) and N=23 is used. FIG. 17A illustrates an intensity of a synthetic transmit focusing beam pattern according to a lateral distance and an axial distance. FIG. 17B is an intensity of a synthetic transmit focusing beam pattern according to a lateral distance.

Referring to FIGS. 17A and 17B, two grating lobes are located in an ROI (−20 mm<x<20 mm), and an intensity of each of the two grating lobes is almost the same as an intensity of a main lobe. Thus, the quality of an ultrasound image may be reduced.

FIGS. 18A and 18B illustrate a synthetic transmit focusing beam pattern when a plane wave combination including a plurality of plane wave sets having Δα=0.406, 0.207, 0.139. 0.084, 0.060 (24°, 12°, 8°, 4.8°, 3.43°) and N=2, 3, 4, 6, 8 (23 in total) is used. FIG. 18A illustrates an intensity of a synthetic transmit focusing beam pattern according to a lateral distance and an axial distance. FIG. 18B illustrates an intensity of a synthetic transmit focusing beam pattern according to a lateral distance. Positions of grating lobes of plane wave sets having different intervals Δα are different from one another. Although main lobes of the plane wave sets overlap one another and thus intensities of the main lobes are increased, since the grating lobes of the plane wave sets do not overlap one another, intensities of the grating lobes are reduced to be less than those of the main lobes.

Accordingly, the quality of an ultrasound image when the plurality of intervals Δα are used as shown in FIGS. 18A and 18B may be higher than the quality of an ultrasound image when one interval Δα is used as shown in FIGS. 17A and 17B.

Figure 19A:
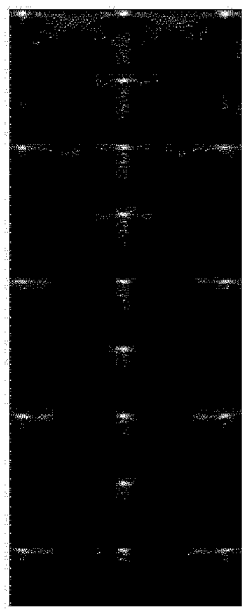
FIGS. 19A and 19B are views of an ultrasound image according to some exemplary embodiments.
Figure 19B:
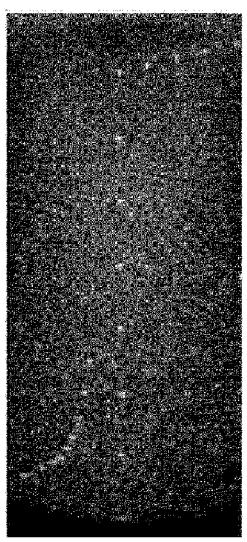

FIGS. 19A and 19B are views of an ultrasound image according to some exemplary embodiments.

FIG. 19A illustrates a simulation result of a plane ultrasound image synthesized by reducing an intensity of a grating lobe according to some exemplary embodiments. FIG. 19B is an actual plane ultrasound image of a human phantom synthesized by reducing an intensity of a grating lobe.

Figure 20A:
FIGS. 20A and 20B are views of an ultrasound image according to comparative examples.
Figure 20B:
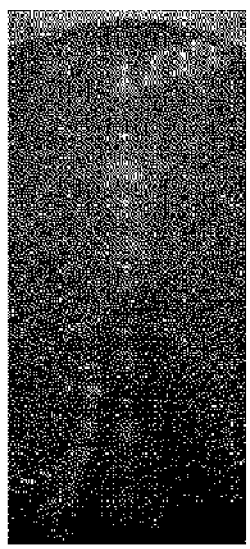

FIGS. 20A and 20B are views of an ultrasound image according to comparative examples.

FIG. 20A illustrates a simulation result of a plane ultrasound image synthesized without considering a grating lobe. FIG. 20B is an actual ultrasound image of a human phantom synthesized without considering a grating lobe.

In FIGS. 20A and 20B, it is found that artifacts occur around bright points in an image that is a point target due to the effect of a grating lobe, unlike in FIGS. 19A and 19B.

According to some exemplary embodiments, the quality of an ultrasound image using plane waves may be improved. An SNR and a contrast ratio of an ultrasound image may be increased and artifacts may be removed or reduced in the ultrasound image by allowing a grating lobe that causes image quality degradation to be located outside an ROI or reducing an intensity of a grating lobe relative to a main lobe.

Some of the above exemplary embodiments have been performed in the ultrasound diagnosis apparatus 100 of FIGS. 1 and 2. However, the some exemplary embodiments may be performed even in an ultrasound probe, instead of the ultrasound diagnosis apparatus 100. An ultrasound probe according to some exemplary embodiments will now be explained.

Figure 21:
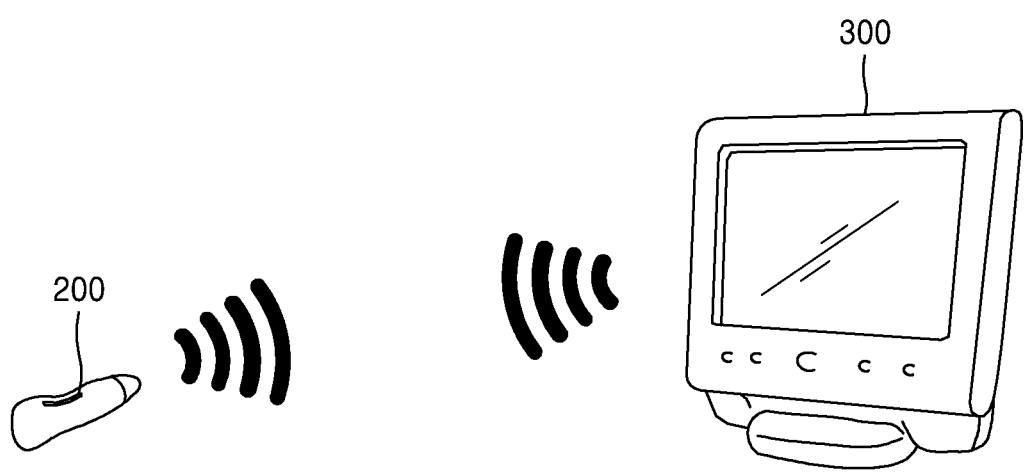
FIG. 21 is a view for explaining an ultrasound probe according to some exemplary embodiments.

FIG. 21 is a view for explaining an ultrasound probe 200 according to some exemplary embodiments.

Referring to FIG. 21, the ultrasound probe 200 may be wirelessly connected to a medical imaging apparatus 300. The ultrasound probe 200 may be referred to as a "wireless probe".

The ultrasound probe 200 transmits ultrasound signals to the object 10 and receives echo signals reflected from the object 10. The ultrasound probe 200 may generate ultrasound data from the echo signals. The ultrasound probe 200 may generate an ultrasound image based on the ultrasound data. The ultrasound probe 200 may wirelessly transmit the ultrasound data or the ultrasound image to the medical imaging apparatus 300.

The medical imaging apparatus 300 may display the ultrasound image based on the ultrasound data or the ultrasound image received from the ultrasound probe 200. The medical imaging apparatus 300 may be any apparatus that may be wirelessly connected to the ultrasound probe 200 and may display the ultrasound image. The medical imaging apparatus 300 may be the ultrasound diagnosis apparatus 100 of FIGS. 1 and 2.

Figure 22:
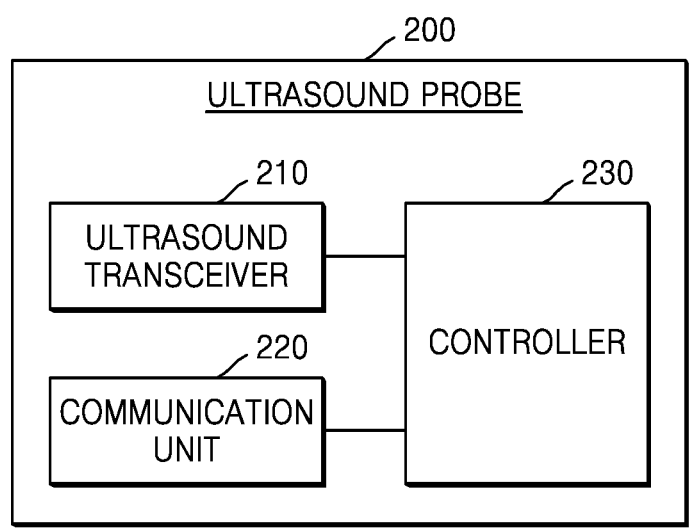
FIG. 22 is a block diagram showing a configuration of the ultrasound probe according to some exemplary embodiments.

FIG. 22 is a block diagram showing a configuration of the ultrasound probe 200 according to some exemplary embodiments.

Referring to FIG. 22, the ultrasound probe 200 may include an ultrasound transceiver 210, a communication unit 220, and a controller 230.

The controller 230 may perform an operation similar to an operation performed by the controller 120 of the ultrasound diagnosis apparatus 100.

The controller 230 may determine a plurality of plane waves according to at least one of the first exemplary embodiment and the second exemplary embodiment. The above description may apply, and thus a repeated explanation will not be given.

The controller 230 may control the ultrasound transceiver 210 to transmit the plurality of plane waves determined by the controller 230.

The ultrasound transceiver 210 may transmit the plurality of plane waves and may receive echo signals under the control of the controller 230.

The controller 230 may apply an apodization window having a low side lobe to the echo signals. The controller 230 may generate ultrasound data by focusing the echo signals. The controller 230 may obtain an ultrasound image based on the ultrasound data.

The controller 230 may control the communication unit 220 to transmit the ultrasound data or the ultrasound image to the medical imaging apparatus 300 through the communication unit 220.

The communication unit 220 may include a wireless communication module so that the ultrasound probe 200 wirelessly communications with the medical imaging apparatus 300.

Figure 23:
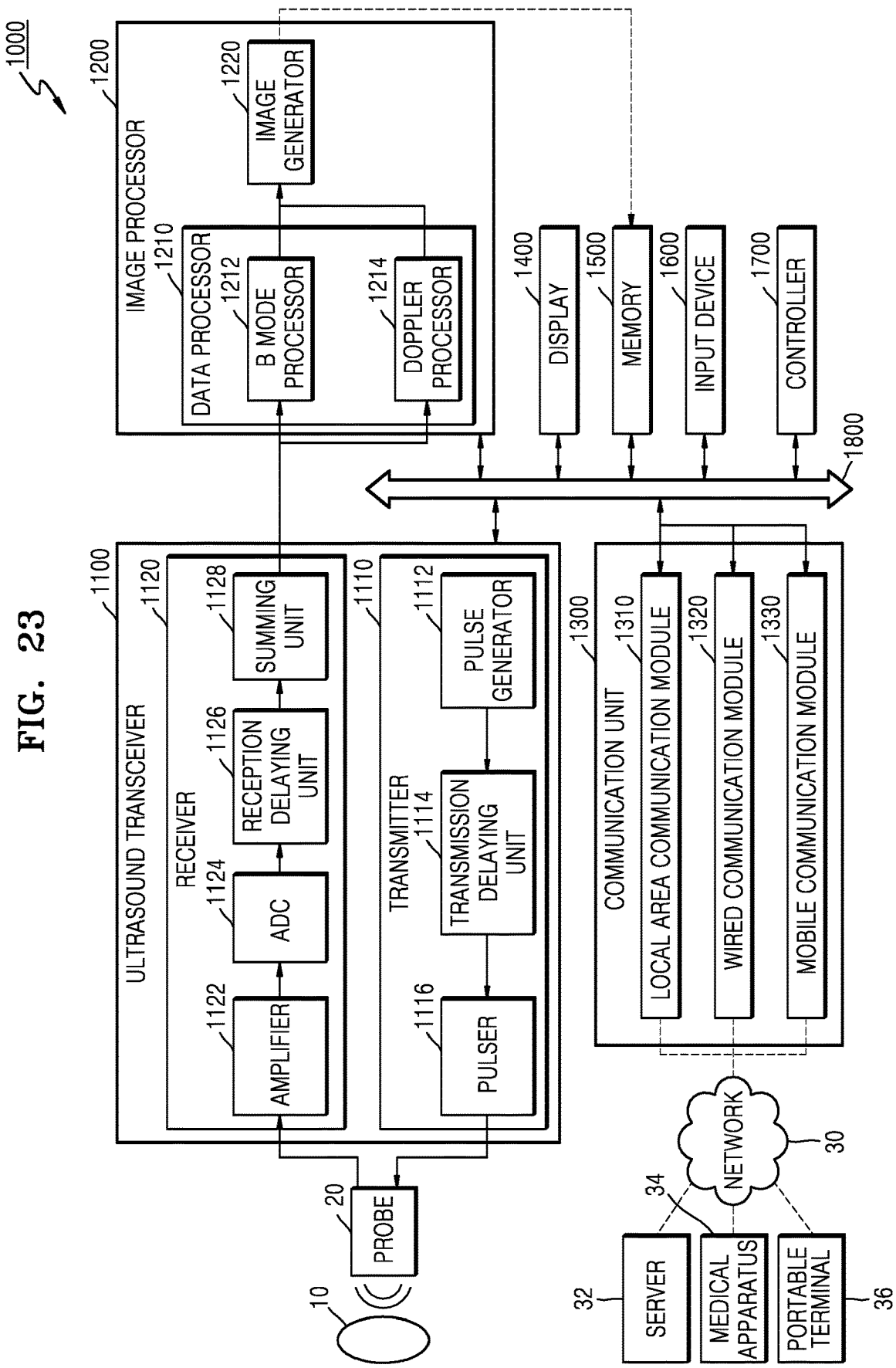
FIG. 23 is a block diagram showing a configuration of an ultrasound diagnosis apparatus according to some exemplary embodiments.

FIG. 23 is a block diagram showing a configuration of an ultrasound diagnosis apparatus 1000 according to some exemplary embodiments. Referring to FIG. 23, the ultrasound diagnosis apparatus 1000 may include a probe 20, an ultrasound transceiver 1100, an image processor 1200, a communication unit 1300, a display 1400, a memory 1500, an input device 1600, and a controller 1700, which may be connected to one another via buses 1800.

The ultrasound diagnosis apparatus 1000 of FIG. 23 may be some exemplary embodiments of the ultrasound diagnosis apparatus 100 of FIGS. 1 and 2. The probe 20 and the controller 1700 of the ultrasound diagnosis apparatus 1000 correspond to the probe 110 and the controller 120 of the ultrasound diagnosis apparatus 100 of FIG. 2, and thus a repeated explanation thereof will not be given.

The ultrasound diagnosis apparatus 1000 may be a cart type apparatus or a portable type apparatus. Examples of portable ultrasound diagnosis apparatuses may include, but are not limited to, a PACS viewer, a smartphone, a laptop computer, a PDA, and a tablet PC.

The probe 20 transmits ultrasound waves to the object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly. According to some exemplary embodiments, the ultrasound diagnosis apparatus 1000 may include a plurality of the probes 20.

The probe 20 according to some exemplary embodiments may transmit a plurality of plane waves at a plurality of steering angles.

A transmitter 1110 applies a driving signal to the probe 20. The transmitter 1110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 1120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion on the amplified echo signals. The reception delaying unit 1126 delays digital echo signals output by the ADC 1124 by delay times necessary for determining reception directionality, and the summing unit 1128 generates ultrasound data by summing the echo signals processed by the reception delaying unit 1126. Also, according to some exemplary embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 in a data processor 1210 extracts B mode components from ultrasound data and processes the B mode components. An image generator 1220 may generate an ultrasound image indicating signal intensities as brightness based on the extracted B mode components.

Similarly, a Doppler processor 1214 in the data processor 1210 may extract Doppler components from ultrasound data, and the image generator 1220 may generate a Doppler image indicating a movement of an object as colors or waveforms based on the extracted Doppler components.

According to some exemplary embodiments, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

The display 1400 displays the generated ultrasound image. The display 1400 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 1400 according to some exemplary embodiments.

The communication unit 1300 is connected to a network 30 by wire or wirelessly to communicate with an external device or a server. The communication unit 1300 may exchange data with a hospital server or another medical apparatus in a hospital, which is connected thereto via a PACS. Furthermore, the communication unit 1300 may perform data communication according to the digital imaging and communications in medicine (DICOM) standard.

The communication unit 1300 may transmit or receive data related to diagnosis of an object, e.g., an ultrasound image, ultrasound data, and Doppler data of the object, via the network 30 and may also transmit or receive medical images captured by another medical apparatus 34, e.g., a computed tomography (CT) apparatus, a magnetic resonance imaging (MRI) apparatus, or an X-ray apparatus. Furthermore, the communication unit 1300 may receive information about a diagnosis history or medical treatment schedule of a patient from a server and utilizes the received information to diagnose the patient. Furthermore, the communication unit 1300 may perform data communication not only with a server or a medical apparatus in a hospital, but also with a portable terminal of a medical doctor or patient.

The communication unit 1300 is connected to the network 30 by wire or wirelessly to exchange data with a server 32, the medical apparatus 34, or a portable terminal 36. The communication unit 1300 may include one or more components for communication with external devices. For example, the communication unit 1300 may include a local area communication module 1310, a wired communication module 1320, and a mobile communication module 1330.

The local area communication module 1310 refers to a module for local area communication within a predetermined distance. Examples of local area communication techniques according to some exemplary embodiments may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to some exemplary embodiments may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000. For example, the memory 1500 may store medical data related to diagnosis of an object, such as ultrasound data and an ultrasound image that are input or output, and may also store algorithms or programs which are to be executed in the ultrasound diagnosis apparatus 1000.

The memory 1500 may be any of various storage media, e.g., a flash memory, a hard disk drive, electrically erasable programmable read-only memory (EEPROM), etc. Furthermore, the ultrasound diagnosis apparatus 1000 may utilize web storage or a cloud server that performs the storage function of the memory 1500 online.

The input device 1600 refers to a means via which a user inputs data for controlling the ultrasound diagnosis apparatus 1000. The input device 1600 may include hardware components, such as a keypad, a mouse, a touch pad, a touch screen, and a jog switch. However, exemplary embodiments of the inventive concept are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound diagnosis apparatus 1000. In other words, the controller 1700 may control operations among the probe 20, the ultrasound transceiver 1100, the image processor 1200, the communication unit 1300, the display 1400, the memory 1500, and the input device 1600 of FIG. 23.

The controller 1700 may perform the above operations according to some exemplary embodiments.

The controller 1700 may determine a plurality of plane waves so that a grating lobe of a synthetic transmit focusing beam pattern using the plurality of plane waves is located outside an ROI according to the first exemplary embodiment.

Alternatively, the controller 1700 may determine a plurality of plane waves so that an intensity of a grating lobe is less than an intensity of a main lobe in a synthetic transmit focusing beam pattern using the plurality of plane waves according to the second exemplary embodiment.

Alternatively, the controller 1700 may determine a plurality of plane waves according to at least one of the first exemplary embodiment and the second exemplary embodiment.

The first exemplary embodiment and the second exemplary embodiment have been described above, and thus a repeated explanation thereof will not be given.

The controller 1700 may apply an apodization window having a low side lobe to echo signals.

All or some of the probe 20, the ultrasound transceiver 1100, the image processor 1200, the communication unit 1300, the display 1400, the memory 1500, the input device 1600, and the controller 1700 may be implemented as software modules. However, exemplary embodiments of the inventive concept are not limited thereto, and some of the components stated above may be implemented as hardware modules. Furthermore, at least one selected from the ultrasound transceiver 1100, the image processor 1200, and the communication unit 1300 may be included in the controller 1700. However, exemplary embodiments of the inventive concept are not limited thereto.

Figure 24:
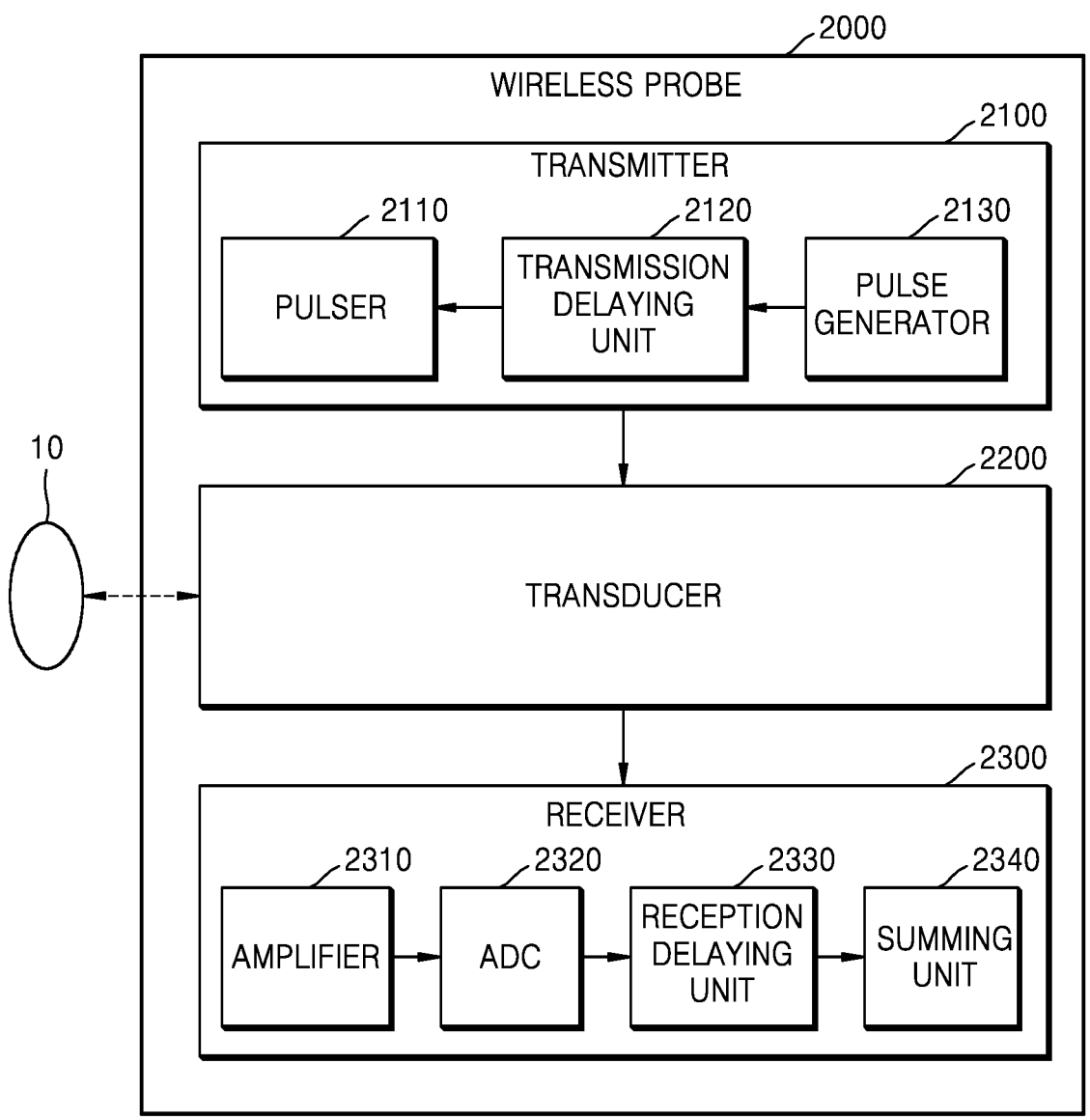
FIG. 24 is a block diagram showing a configuration of a wireless probe according to some exemplary embodiments.

FIG. 24 is a block diagram showing a configuration of a wireless probe 2000 according to some exemplary embodiments. As described above with reference to FIG. 23, the wireless probe 2000 may include a plurality of transducers, and, according to some exemplary embodiments of the inventive concept, may include some or all of the components of the ultrasound transceiver 1000 of FIG. 23.

The wireless probe 2000 of FIG. 24 according to some exemplary embodiments may include a transmitter 2100, a transducer 2200, and a receiver 2300. Since descriptions thereof are given above with reference to FIG. 23, detailed descriptions thereof will be omitted here. In addition, according to some exemplary embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound diagnosis apparatus 1000 shown in FIG. 23.

The wireless probe 2000 of FIG. 24 may be some exemplary embodiments of the ultrasound transceiver 210 of the ultrasound probe 200 of FIG. 22, and thus a repeated explanation thereof will not be given. The wireless probe 2000 of FIG. 24 may further include the communication unit 220 and the controller 230, like in FIG. 22.

Figure 25:
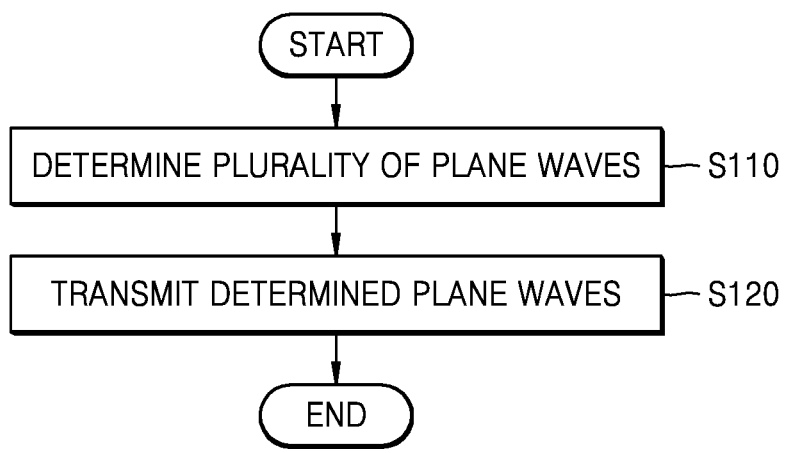
FIG. 25 is a flowchart of a method of controlling an ultrasound probe, according to some exemplary embodiments.

FIG. 25 is a flowchart of a method of controlling an ultrasound probe according to some exemplary embodiments.

Referring to FIG. 25, in operation S110, an ultrasound system may determine a plurality of plane waves to be transmitted at a plurality of steering angles by using the ultrasound probe. The plurality of plane waves may be determined according to at least one of the first exemplary embodiment and the second exemplary embodiment. The plurality of plane waves are determined in the first exemplary embodiment so that a grating lobe of a synthetic transmit focusing beam pattern is located outside an ROI and the plurality of plane waves are determined in the second exemplary embodiment so that an intensity of a grating lobe is less than an intensity of a main lobe in a synthetic transmit focusing beam pattern. The first exemplary embodiment and the second exemplary embodiment have been described above, and thus a repeated explanation thereof will not be given.

In operation S120, the ultrasound system may transmit the determined plurality of plane waves through the ultrasound probe.

The ultrasound system that performs the method of controlling the ultrasound probe of FIG. 25 may be the ultrasound diagnosis apparatus 100 or 1000 or the ultrasound probe 200 or 2000. Each operation of the method of controlling the ultrasound probe of FIG. 25 may be performed in a manner as described above.

The above some exemplary embodiments may be embodied as a program executed in a computer, and may be implemented in a general-purpose digital computer for executing the program by using a non-transitory computer-readable recording medium.

Examples of the computer-readable recording medium include storage media such as magnetic storage media (e.g., read-only memories (ROMs), floppy discs, or hard discs), optically readable media (e.g., compact disk-read only memories (CD-ROMs), or digital versatile disks (DVDs)), etc.

While the inventive concept has been particularly shown and described with reference to exemplary embodiments thereof, they are provided for the purposes of illustration and it will be understood by one of ordinary skill in the art that various modifications and equivalent other embodiments can be made from the inventive concept. Accordingly, the true technical scope of the inventive concept is defined by the technical spirit of the appended claims.

The invention claimed is:

1. An ultrasound diagnosis apparatus comprising:
   a probe configured to transmit a plurality of plane waves comprising a plurality of plane wave sets, at a plurality of steering angles, each plane wave of the plurality of plane waves corresponding to a unique steering angle of the plurality of steering angles; and
   a processor configured to determine a number of the plurality of plane waves so that a grating lobe of a synthetic transmit focusing beam pattern using the plurality of plane waves is located outside a region of interest,
   wherein intervals between sine values of the plurality of steering angles of the plurality of plane wave sets are different from one another.

2. The ultrasound diagnosis apparatus of claim 1, wherein the processor is further configured to determine the number of the plurality of plane waves so that an interval between sine values of the plurality of steering angles corresponding to each plane wave of the plurality of plane waves is equal to or less than a first reference value.

3. The ultrasound diagnosis apparatus of claim 2, wherein the processor is further configured to set the first reference value as a value obtained by dividing a wavelength of the plurality of plane waves by a size of an aperture of the probe.

4. The ultrasound diagnosis apparatus of claim 1, wherein the processor is further configured to:
   fix a minimum steering angle and a maximum steering angle, and
   determine the number of the plurality of plane waves so that a number of the plurality of steering angles corresponding to the number of the plurality of planes waves is equal to or greater than a second reference value.

5. The ultrasound diagnosis apparatus of claim 1, wherein the processor is further configured to adjust a size of the region of interest so that the grating lobe is located outside the region of interest.

6. The ultrasound diagnosis apparatus of claim 1, wherein the probe receives echo signals, and
   wherein the processor is further configured to apply an apodization window having a low side lobe to the echo signals.

7. The ultrasound diagnosis apparatus of claim 1, wherein the processor is further configured to determine the number of the plurality of plane waves so that an intensity of the grating lobe is less than an intensity of a main lobe in the synthetic transmit focusing beam pattern using the plurality of plane waves.

8. The ultrasound diagnosis apparatus of claim 7,
   wherein each plane wave set of the plurality of plane wave sets has an associated grating lobe, and
   wherein grating lobes of the plurality of plane wave sets do not overlap one another.

9. The ultrasound diagnosis apparatus of claim 7,
   wherein each of the plurality of plane wave sets comprises a second number of plane waves transmitted at a second number of steering angles.

10. The ultrasound diagnosis apparatus of claim 7, wherein minimum steering angles and maximum steering angles of the plurality of plane wave sets are the same, and numbers of the steering angles of the plurality of plane wave sets are different from one another.

11. The ultrasound diagnosis apparatus of claim 7, wherein the plurality of steering angles of the plurality of plane waves determined by the processor are arbitrary.

12. The ultrasound diagnosis apparatus of claim 7,
    wherein intervals of the plurality of steering angles of the plurality of plane wave sets are different from one another within each of the plurality of plane wave sets and between each of the plurality of plane wave sets.

13. A method of controlling an ultrasound probe, the method comprising:
    determining a number of a plurality of plane waves so that a grating lobe of a synthetic transmit focusing beam pattern using the plurality of plane waves, comprising a plurality of plane wave sets, to be transmitted by the ultrasound probe at a plurality of steering angles is located outside a region of interest, each plane wave of the plurality of plane waves corresponding to a unique steering angle of the plurality of steering angles; and
    transmitting, by the ultrasound probe, the determined number of the plurality of plane waves,
    wherein intervals between sine values of the plurality of steering angles of the plurality of plane wave sets are different from one another.

14. The method of claim 13, wherein the determining of the number of the plurality of plane waves comprises determining the number of the plurality of plane waves so that an intensity of the grating lobe is less than an intensity of a main lobe in the synthetic transmit focusing beam pattern.

15. A non-transitory computer-readable recording medium having embodied thereon a program for executing the method of claim 13.

* * * * *